United States Patent
Mannerloef et al.

(10) Patent No.: US 6,531,649 B1
(45) Date of Patent: *Mar. 11, 2003

(54) TRANSGENIC SUGAR BEET PLANT EXPRESSING CP4/EPSPS ENZYME ACTIVITY

(75) Inventors: Marie Mannerloef, Helsingborg (SE); Paul Peter Tenning, Helsingborg (SE); Per Steen, Stubbekoebing (DK)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,039

(22) Filed: Nov. 4, 1999

Related U.S. Application Data

(63) Continuation of application No. 09/182,117, filed on Oct. 29, 1998, now Pat. No. 6,204,436.
(60) Provisional application No. 60/112,003, filed on Oct. 31, 1997.

(51) Int. Cl.[7] .......... C12N 15/82; C12N 15/84; C12N 15/90; A01H 5/00; A01H 5/10

(52) U.S. Cl. .......... 800/300; 435/469; 800/294

(58) Field of Search .......... 435/418, 419, 435/69.1, 320.1, 410, 468, 469; 800/238, 288, 294, 300, 295, 298

Primary Examiner—Amy J. Nelson
Assistant Examiner—Ashwin Mehta
(74) Attorney, Agent, or Firm—Bruce Vrana

(57) ABSTRACT

The present invention relates to transgenic sugar beet plants which due to the expression of cp4/epsps enzyme activity tolerate treatment with about 4 to about 18 liters Roundup® per hectar. The plants can be characterized by theis specific integration site. The invention further relates to seeds obtained from said plants and a method for producing said plants.

10 Claims, No Drawings

SEQUENCE LISTING

<160> NUMBER OF SEQ ID NOS: 36

<210> SEQ ID NO 1
<211> LENGTH: 8012
<212> TYPE: DNA
<213> ORGANISM: Sugar beet

<400> SEQUENCE: 1

```
aacgacaatc tgatccccat caagcttgag ctcaggattt agcagcattc cagattgggt      60
tcaatcaaca aggtacgagc catatcactt tattcaaatt ggtatcgcca aaaccaagaa     120
ggaactccca tcctcaaagg tttgtaagga agaattctca gtccaaagcc tcaacaaggt     180
cagggtacag agtctccaaa ccattagcca aaagctacag gagatcaatg aagaatcttc     240
aatcaaagta aactactgtt ccagcacatg catcatggtc agtaagtttc agaaaaagac     300
atccaccgaa gacttaaagt tagtgggcat ctttgaaagt aatcttgtca acatcgagca     360
gctggcttgt ggggaccaga caaaaaagga atggtgcaga attgttaggc gcacctacca     420
aaagcatctt tgcctttatt gcaaagataa agcagattcc tctagtacaa gtggggaaca     480
aaataacgtg gaaagagct gtcctgacag cccactcact aatgcgtatg acgaacgcag     540
tgacgaccac aaaagaattc cctctatata agaaggcatt cattcccatt tgaaggatca     600
tcagatactg aaccaatcct tctagaagat ctaagcttat cgataagctt gatgtaattg     660
gaggaagatc aaaattttca atccccattc ttcgattgct tcaattgaag tttctccgat     720
ggcgcaagtt agcagaatct gcaatggtgt gcagaaccca tctcttatct ccaatctctc     780
gaaatccagt caacgcaaat ctcccttatc ggtttctctg aagacgcagc agcatccacg     840
agcttatccg atttcgtcgt cgtggggatt gaagaagagt gggatgacgt taattggctc     900
```

```
tgagcttcgt cctcttaagg tcatgtcttc tgtttccacg gcgtgcatgc ttcacggtgc      960
aagcagccgt ccagcaactg ctcgtaagtc ctctggtctt tctggaaccg tccgtattcc     1020
aggtgacaag tctatctccc acaggtcctt catgtttgga ggtctcgcta gcggtgaaac     1080
tcgtatcacc ggtctttttgg aaggtgaaga tgttatcaac actggtaagg ctatgcaagc    1140
tatgggtgcc agaatccgta aggaaggtga tacttggatc attgatggtg ttggtaacgg     1200
tggactcctt gctcctgagg ctcctctcga tttcggtaac gctgcaactg gttgccgttt     1260
gactatgggt cttgttggtg tttacgattt cgatagcact ttcattggtg acgcttctct     1320
cactaagcgt ccaatgggtc gtgtgttgaa cccacttcgc gaaatgggtg tgcaggtgaa     1380
gtctgaagac ggtgatcgtc ttccagttac cttgcgtgga ccaaagactc caacgccaat     1440
cacctacagg gtacctatgg cttccgctca agtgaagtcc gctgttctgc ttgctggtct     1500
caacacccca ggtatcacca ctgttatcga gccaatcatg actcgtgacc acactgaaaa     1560
gatgcttcaa ggttttggtg ctaaccttac cgttgagact gatgctgacg gtgtgcgtac     1620
catccgtctt gaaggtcgtg gtaagctcac cggtcaagtg attgatgttc aggtgatcc      1680
atcctctact gctttcccat tggttgctgc cttgcttgtt ccaggttccg acgtcaccat     1740
ccttaacgtt tgatgaacc caacccgtac tggtctcatc ttgactctgc aggaaatggg     1800
tgccgacatc gaagtgatca acccacgtct tgctggtgga gaagacgtgg ctgacttgcg     1860
tgttcgttct tctactttga agggtgttac tgttccagaa gaccgtgctc cttctatgat     1920
cgacgagtat ccaattctcg ctgttgcagc tgcattcgct gaaggtgcta ccgttatgaa     1980
cggtttggaa gaactccgtg ttaaggaaag cgaccgtctt tctgctgtcg caaacggtct     2040
caagctcaac ggtgttgatt gcgatgaagg tgagacttct ctcgtcgtgc gtggtcgtcc     2100
tgacggtaag ggtctcggta acgcttctgg agcagctgtc gctacccacc tcgatcaccg     2160
tatcgctatg agcttcctcg ttatgggtct cgtttctgaa acccctgtta ctgttgatga     2220
tgctactatg atcgctacta gcttcccaga gttcatggat tgatggctg gtcttggagc      2280
taagatcgaa ctctccgaca ctaaggctgc ttgatgagct caagaattcg agctcggtac     2340
cggatcctct agctagagct ttcgttcgta tcatcggttt cgacaacgtt cgtcaagttc     2400
aatgcatcag tttcattgcg cacacaccag aatcctactg agttcgagta ttatggcatt     2460
gggaaaactg ttttttcttgt accatttgtt gtgcttgtaa tttactgtgt tttttattcg     2520
gttttcgcta tcgaactgtg aaatggaaat ggatggagaa gagttaatga atgatatggt     2580
ccttttgttc attctcaaat taatattatt tgtttttttct cttattttgtt gtgtgttgaa    2640
tttgaaatta aagagatat gcaaacattt tgttttgagt aaaaatgtgt caaatcgtgg      2700
cctctaatga ccgaagttaa tatgaggagt aaaacacttg tagttgtacc attatgctta     2760
ttcactaggc aacaaatata ttttcagacc tagaaaagct gcaaatgtta ctgaatacaa     2820
gtatgtcctc ttgtgttttta gacatttatg aactttcctt tatgtaattt tccagaatcc    2880
ttgtcagatt ctaatcattg ctttataatt atagttatac tcatggattt gtagttgagt    2940
atgaaaatat tttttaatgc attttatgac ttgccaattg attgacaaca tgcatcaatc    3000
gacctgcagc cactcgaagc ggccgcgttc aagcttctgc aggtccgatg tgagactttt   3060
caacaaaggg taatatccgg aaacctcctc ggattccatt gcccagctat ctgtcacttt   3120
attgtgaaga tagtggaaaa ggaaggtggc tcctacaaat gccatcattg cgataaagga   3180
aaggccatcg ttgaagatgc ctctgccgac agtggtccca aagatggacc cccacccacg   3240
```

```
aggagcatcg tggaaaaaga agacgttcca accacgtctt caaagcaagt ggattgatgt    3300
gatggtccga tgtgagactt ttcaacaaag gtaatatcc ggaaacctcc tcggattcca     3360
ttgcccagct atctgtcact ttattgtgaa gatagtggaa aaggaaggtg gctcctacaa    3420
atgccatcat tgcgataaag gaaaggccat cgttgaagat gcctctgccg acagtggtcc    3480
caaagatgga cccccaccca cgaggagcat cgtggaaaaa aagacgttc caaccacgtc     3540 ttcaaagcaa gtggattgat gtgatatctc cactgacgta agggatgacg cacaatccca    3600
ctatccttcg caagacccctt cctctatata aggaagttca tttcatttgg agaggacacg   3660
ctgacaagct gactctagca gatctccatg gtccgtcctg tagaaacccc aacccgtgaa    3720
atcaaaaaac tcgacggcct gtgggcattc agtctggatc gcgaaaactg tggaattgat    3780
cagcgttggt gggaaagcgc gttacaagaa agccgggcaa ttgctgtgcc aggcagtttt    3840
aacgatcagt tcgccgatgc agatattcgt aattatgcgg gcaacgtctg gtatcagcgc    3900
gaagtcttta taccgaaagg ttgggcaggc cagcgtatcg tgctgcgttt cgatgcggtc    3960
actcattacg gcaaagtgtg ggtcaataat caggaagtga tggagcatca gggcggctat    4020
acgccatttg aagccgatgt cacgccgtat gttattgccg ggaaaagtgt acgtatcacc    4080
gtttgtgtga acaacgaact gaactggcag actatcccgc cgggaatggt gattaccgac    4140
gaaaacggca agaaaaagca gtcttacttc catgatttct ttaactatgc cggaatccat    4200
cgcagcgtaa tgctctacac cacgccgaac acctgggtgg acgatatcac cgtggtgacg    4260
catgtcgcgc aagactgtaa ccacgcgtct gttgactggc aggtggtggc caatggtgat    4320
gtcagcgttg aactgcgtga tgcggatcaa caggtggttg caactggaca aggcactagc    4380
gggactttgc aagtggtgaa tccgcacctc tggcaaccgg gtgaaggtta tctctatgaa    4440
ctgtgcgtca cagccaaaag ccagacagag tgtgatatct acccgcttcg cgtcggcatc    4500
cggtcagtgg cagtgaaggg cgaacagttc ctgattaacc acaaaccgtt ctactttact    4560
ggctttggtc gtcatgaaga tgcggactta cgtggcaaag gattcgataa cgtgctgatg    4620
gtgcacgacc acgcattaat ggactggatt ggggccaact cctaccgtac ctcgcattac    4680
ccttacgctg aagagatgct cgactgggca gatgaacatg gcatcgtggt gattgatgaa    4740
actgctgctg tcggctttaa cctctcttta ggcattggtt tcgaagcggg caacaagccg    4800
aaagaactgt acagcgaaga ggcagtcaac ggggaaactc agcaagcgca cttacaggcg    4860
attaaagagc tgatagcgcg tgacaaaaac cacccaagcg tggtgatgtg gagtattgcc    4920
aacgaaccgg atacccgtcc tgcacgggaa tatttcggca tttcgccact ggcggaagca    4980
acgcgtaaac tcgacccgac gcgtccgatc acctgcgtca atgtaatgtt ctgcgacgct    5040
cacaccgata ccatcagcga tctctttgat gtgctgtgcc tgaaccgtta ttacggatgg    5100
tatgtccaaa gcggcgattt ggaaacggca gagaaggtac tggaaaaaga acttctggcc    5160
tggcaggaga aactgcatca gccgattatc atcaccgaat acggcgtgga tacgttagcc    5220
gggctgcact caatgtacac cgacatgtgg agtgaagagt atcagtgtgc atggctggat    5280
atgtatcacc gcgtctttga tcgcgtcagc gccgtcgtcg gtgaacaggt atggaatttc    5340
gccgattttg cgacctcgca aggcatattg cgcgttggcg gtaacaagaa agggatcttc    5400
actcgcgacc gcaaaccgaa gtcggcggct tttctgctgc aaaaacgctg gactggcatg    5460
aacttcggtg aaaaaccgca gcagggaggc aaacaatgaa tcaacaactc tcctggcgca    5520
ccatcgtcgg ctacagcctc ggtgggaat tcgagctcgc ccgggatcc tctagctaga    5580 gctttcgttc gtatcatcgg tttcgacaac gttcgtcaag ttcaatgcat cagtttcatt    5640
```

```
gcgcacacac cagaatccta ctgagttcga gtattatggc attgggaaaa ctgttttct    5700 tgtaccattt gttgtgcttg taatttactg tgtttttat tcggttttcg ctatcgaact    5760
gtgaaatgga aatggatgga gaagagttaa tgaatgatat ggtccttttg ttcattctca    5820
aattaatatt atttgttttt tctcttattt gttgtgtgtt gaatttgaaa ttataagaga    5880
tatgcaaaca ttttgttttg agtaaaaatg tgtcaaatcg tggcctctaa tgaccgaagt    5940
taatatgagg agtaaaacac ttgtagttgt accattatgc ttattcacta ggcaacaaat    6000
atattttcag acctagaaaa gctgcaaatg ttactgaata caagtatgtc ctcttgtgtt    6060
ttagacattt atgaactttc ctttatgtaa ttttccagaa tccttgtcag attctaatca    6120
ttgctttata attatagtta tactcatgga tttgtagttg agtatgaaaa tattttttaa    6180
tgcattttat gacttgccaa ttgattgaca acatgcatca atcgacctgc agcccaagct    6240
tgagctcagg atttagcagc attccagatt gggttcaatc aacaaggtac gagccatatc    6300
actttattca aattggtatc gccaaaacca agaaggaact cccatcctca aggtttgta     6360 aggaagaatt ctcagtccaa agcctcaaca aggtcagggt acagagtctc caaaccatta    6420
gccaaaagct acaggagatc aatgaagaat cttcaatcaa agtaaactac tgttccagca    6480
catgcatcat ggtcagtaag tttcagaaaa agacatccac cgaagactta agttagtgg     6540 gcatctttga aagtaatctt gtcaacatcg agcagctggc ttgtggggac cagacaaaaa    6600
aggaatggtg cagaattgtt aggcgcacct accaaaagca tctttgcctt tattgcaaag    6660
ataaagcaga ttcctctagt acaagtgggg aacaaaataa cgtggaaaag agctgtcctg    6720
acagcccact cactatgcg tatgacgaac gcagtgacga ccacaaaaga attccctcta    6780
tataagaagg cattcattcc catttgaagg atcatcagat actgaaccaa tccttctaga    6840
agatctccac aatggcttcc tctatgctct cttccgctac tatggttgcc ctccggctc     6900 aggccactat ggtcgctcct ttcaacggac ttaagtcctc cgctgccttc ccagccaccc    6960
gcaaggctaa caacgacatt acttccatca caagcaacgg cggaagagtt aactgcatgc    7020
aggtgtggcc tccgattgga agaagaagt ttgagactct ctcttacctt cctgaccttta    7080 ccgattccgg tggtcgcgtc aactgcatgc aggccatggc tgagaaccac aagaaggttg    7140
gtatcgctgg agctggaatc gttggtgttt gcactgcttt gatgcttcaa cgtcgtggat    7200
tcaaggttac cttgattgat ccaaacccac caggtgaagg tgcttctttc ggtaacgctg    7260
gttgcttcaa cggttcctcc gttgttccaa tgtccatgcc aggaaacttg actagcgttc    7320
caaagtggct tcttgaccca atgggtccat tgtccatccg tttcagctac tttccaacca    7380
tcatgccttg gttgattcgt ttcttgcttg ctggaagacc aaaacaaggtg aaggagcaag    7440 ctaaggcact ccgtaacctc atcaagtcca ctgtgccttt gatcaagtcc ttggctgagg    7500
aggctgatgc tagccacctt atccgtcacg aaggtcacct taccgtgtac cgtggagaag    7560
cagacttcgc caaggaccgt ggaggttggg aacttcgtcg tctcaacggt gttcgtactc    7620
aaatcctcag cgctgatgca ttgcgtgatt tcgatcctaa cttgtctcac gcctttacca    7680
agggaatcct tatcgaagag aacggtcaca ccatcaaccc acaaggtctc gtgactctct    7740
tgtttcgtcg tttcatcgct aacgtggag agttcgtgtc tgctcgtgtt atcggattcg    7800
agactgaagg tcgtgctctc aagggtatca ccaccaccaa cggtgttctt gctgttgatg    7860
cagctgttgt tgcagctggt gcacactcca agtctcttgc taactccctt ggtgatgaca    7920
tcccattgga taccgaacgt ggataccaca tcgtgatcgc caacccagaa gctgctccac    7980
```

-continued

```
gtattccaac taccgatgct tctggaaagt tc                                    8012

<210> SEQ ID NO 2
<211> LENGTH: 89
<212> TYPE: DNA
<213> ORGANISM: Sugar beet

<400> SEQUENCE: 2
ggattgtgtt tgggttttgt ctgtgtgttt aatgtgttta agggatgaat tagaatgctc       60
ttaatcaacc tacagctgat ttggaccgg                                         89

<210> SEQ ID NO 3
<211> LENGTH: 697
<212> TYPE: DNA
<213> ORGANISM: Sugar beet

<400> SEQUENCE: 3
cggtccaaat tgtttacat tgtgtccaaa tttcggctga tttggacttc cctagctatg        60
ccaactaagc taataaaaaa catgaaacaa caattacaaa ctgtcgagca cccttctac       120 aaactagctt agatttctat tggaagttac aaaacagtaa aactaccaat aggatactaa     180
attaaacata ttaaactatt actcctcaaa agcttgtaca atttgcagaa gaaatgatgg     240
ttgcccaaaa gcttcaaagg gaacctgctg ggaagcctgc tgggacgctg gggatgctgg     300
cagcagcata ccttggcttg aagtactctt ctctcattgg ttttgcttcc cttgcccatg     360
tggtcttcat atggcctcat tacttcccaa gggcttcaaa tcagtaggtg gtggcaacca     420
aaagcatcaa aaacatctcc taaaactagc ttatacaacc ggattacatg agcttatact     480
agcttaactc ttaaagcatg attaacataa tgatgtttaa ggtgtcatta agtattacta     540
atcttgctta agtagagatt aacataggat tagcctaatc aagttgctta agtaaggttt     600
tagaataaac cgagctagtt aggcttaagt agagattaac ataggattag cctaatcaag     660
ttgcttaagt aaggttttag aataaaccga gctagtt                               697

<210> SEQ ID NO 4
<211> LENGTH: 8798
<212> TYPE: DNA
<213> ORGANISM: Sugar beet

<400> SEQUENCE: 4
ggattgtgtt tgggttttgt ctgtgtgttt aatgtgttta agggatgaat tagaatgctc       60
ttaatcaacc tacagctgat ttggaccgga acgacaatct gatccccatc aagcttgagc     120
tcaggattta gcagcattcc agattgggtt caatcaacaa ggtacgagcc atatcacttt     180
attcaaattg gtatcgccaa aaccaagaag gaactcccat cctcaaaggt ttgtaaggaa     240
gaattctcag tccaaagcct caacaaggtc agggtacaga gtctccaaac cattagccaa     300
aagctacagg agatcaatga agaatcttca atcaaagtaa actactgttc cagcacatgc     360
atcatggtca gtaagtttca gaaaaagaca tccaccgaag acttaaagtt agtgggcatc     420
tttgaaagta atcttgtcaa catcgagcag ctggcttgtg gggaccagac aaaaaaggaa     480
tggtgcagaa ttgttaggcg cacctaccaa agcatctttt gcctttattg caaagataaa     540
gcagattcct ctagtacaag tggggaacaa ataacgtgg aaaagagctg tcctgacagc      600
ccactcacta atgcgtatga cgaacgcagt gacgaccaca aaagaattcc ctctatataa     660
gaaggcattc attcccattt gaaggatcat cagatactga accaatcctt ctagaagatc     720
taagcttatc gataagcttg atgtaattgg aggaagatca aaattttcaa tccccattct     780
```

-continued

```
tcgattgctt caattgaagt ttctccgatg gcgcaagtta gcagaatctg caatggtgtg      840
cagaacccat ctcttatctc caatctctcg aaatccagtc aacgcaaatc tcccttatcg      900
gtttctctga agacgcagca gcatccacga gcttatccga tttcgtcgtc gtggggattg      960
aagaagagtg ggatgacgtt aattggctct gagcttcgtc ctcttaaggt catgtcttct     1020
gtttccacgg cgtgcatgct tcacggtgca agcagccgtc cagcaactgc tcgtaagtcc     1080
tctggtcttt ctggaaccgt ccgtattcca ggtgacaagt ctatctccca caggtccttc     1140
atgtttggag gtctcgctag cggtgaaact cgtatcaccg tcttttggaa ggtgaagat     1200 gttatcaaca ctggtaaggc tatgcaagct atgggtgcca gaatccgtaa ggaaggtgat     1260
acttggatca ttgatggtgt tggtaacggt ggactccttg ctcctgaggc tcctctcgat     1320
ttcggtaacg ctgcaactgg ttgccgtttg actatgggtc ttgttggtgt ttacgatttc     1380
gatagcactt tcattggtga cgcttctctc actaagcgtc caatgggtcg tgtgttgaac     1440
ccacttcgcg aaatgggtgt gcaggtgaag tctgaagacg gtgatcgtct tccagttacc     1500
ttgcgtggac caaagactcc aacgccaatc acctacaggg tacctatggc ttccgctcaa     1560
gtgaagtccg ctgttctgct tgctggtctc aacacccag gtatcaccac tgttatcgag     1620
ccaatcatga ctcgtgacca cactgaaaag atgcttcaag ttttggtgc taaccttacc     1680 gttgagactg atgctgacgg tgtgcgtacc atccgtcttg aaggtcgtgg taagctcacc     1740
ggtcaagtga ttgatgttcc aggtgatcca tcctctactg cttcccatt ggttgctgcc     1800 ttgcttgttc caggttccga cgtcaccatc cttaacgttt tgatgaaccc aacccgtact     1860
ggtctcatct tgactctgca ggaaatgggt gccgacatcg aagtgatcaa cccacgtctt     1920
gctggtggag aagacgtggc tgacttgcgt gttcgttctt ctactttgaa gggtgttact     1980
gttccagaag accgtgctcc ttctatgatc gacgagtatc caattctcgc tgttgcagct     2040
gcattcgctg aaggtgctac cgttatgaac ggtttggaag aactccgtgt taaggaaagc     2100
gaccgtcttt ctgctgtcgc aaacggtctc aagctcaacg gtgttgattg cgatgaaggt     2160
gagacttctc tcgtcgtgcg tggtcgtcct gacggtaagg gtctcggtaa cgcttctgga     2220
gcagctgtcg ctacccacct cgatcaccgt atcgctatga gcttcctcgt tatgggtctc     2280
gtttctgaaa accctgttac tgttgatgat gctactatga tcgctactag cttcccagag     2340
ttcatggatt tgatggctgg tcttggagct aagatcgaac tctccgacac taaggctgct     2400
tgatgagctc aagaattcga gctcggtacc ggatcctcta gctagagctt tcgttcgtat     2460
catcggtttc gacaacgttc gtcaagttca atgcatcagt ttcattgcgc acacaccaga     2520
atcctactga gttcgagtat tatggcattg ggaaaactgt ttttcttgta ccatttgttg     2580
tgcttgtaat ttactgtgtt ttttattcgg ttttcgctat cgaactgtga aatggaaatg     2640
gatggagaag agttaatgaa tgatatggtc cttttgttca ttctcaaatt aatattattt     2700
gttttttctc ttatttgttg tgtgttgaat ttgaaattat aagagatatg caaacatttt     2760
gttttgagta aaaatgtgtc aaatcgtggc ctctaatgac cgaagttaat atgaggagta     2820
aaacacttgt agttgtacca ttatgcttat tcactaggca acaaatatat tttcagacct     2880
agaaaagctg caaatgttac tgaatacaag tatgtcctct tgtgttttag acatttatga     2940
actttccttt atgtaatttt ccagaatcct tgtcagattc taatcattgc tttataatta     3000
tagttatact catggatttg tagttgagta tgaaaatatt ttttaatgca ttttatgact     3060
tgccaattga ttgacaacat gcatcaatcg acctgcagcc actcgaagcg gccgcgttca     3120
```

-continued

| | |
|---|---|
| agcttctgca ggtccgatgt gagactttc aacaaagggt aatatccgga aacctcctcg | 3180 |
| gattccattg cccagctatc tgtcacttta ttgtgaagat agtggaaaag gaaggtggct | 3240 |
| cctacaaatg ccatcattgc gataaaggaa aggccatcgt tgaagatgcc tctgccgaca | 3300 |
| gtggtcccaa agatggaccc ccacccacga ggagcatcgt ggaaaagaa gacgttccaa | 3360 |
| ccacgtcttc aaagcaagtg gattgatgtg atggtccgat gtgagacttt tcaacaaagg | 3420 |
| gtaatatccg gaaacctcct cggattccat tgcccagcta tctgtcactt tattgtgaag | 3480 |
| atagtggaaa aggaaggtgg ctcctacaaa tgccatcatt gcgataaagg aaaggccatc | 3540 |
| gttgaagatg cctctgccga cagtggtccc aaagatggac ccccacccac gaggagcatc | 3600 |
| gtggaaaaag aagacgttcc aaccacgtct caaagcaag tggattgatg tgatatctcc | 3660 |
| actgacgtaa gggatgacgc acaatcccac tatccttcgc aagacccttc ctctatataa | 3720 |
| ggaagttcat ttcatttgga gaggacacgc tgacaagctg actctagcag atctccatgg | 3780 |
| tccgtcctgt agaaaccca acccgtgaaa tcaaaaaact cgacggcctg tgggcattca | 3840 |
| gtctggatcg cgaaaactgt ggaattgatc agcgttggtg ggaaagcgcg ttacaagaaa | 3900 |
| gccgggcaat tgctgtgcca ggcagtttta acgatcagtt cgccgatgca gatattcgta | 3960 |
| attatgcggg caacgtctgg tatcagcgcg aagtctttat accgaaaggt tgggcaggcc | 4020 |
| agcgtatcgt gctgcgtttc gatgcggtca ctcattacgg caaagtgtgg gtcaataatc | 4080 |
| aggaagtgat ggagcatcag gcggctata cgccatttga agccgatgtc acgccgtatg | 4140 |
| ttattgccgg gaaaagtgta cgtatcaccg tttgtgtgaa caacgaactg aactggcaga | 4200 |
| ctatcccgcc gggaatggtg attaccgacg aaaacggcaa gaaaaagcag tcttacttcc | 4260 |
| atgatttctt taactatgcc ggaatccatc gcagcgtaat gctctacacc acgccgaaca | 4320 |
| cctgggtgga cgatatcacc gtggtgacgc atgtcgcgca agactgtaac cacgcgtctg | 4380 |
| ttgactggca ggtggtggcc aatggtgatg tcagcgttga actgcgtgat gcggatcaac | 4440 |
| aggtggttgc aactggacaa ggcactagcg ggactttgca agtggtgaat ccgcacctct | 4500 |
| ggcaaccggg tgaaggttat ctctatgaac tgtgcgtcac agccaaaagc cagacagagt | 4560 |
| gtgatatcta cccgcttcgc gtcggcatcc ggtcagtggc agtgaagggc aacagttcc | 4620 |
| tgattaacca caaaccgttc tactttactg gctttggtcg tcatgaagat gcggacttac | 4680 |
| gtggcaaagg attcgataac gtgctgatgg tgcacgacca cgcattaatg gactggattg | 4740 |
| gggccaactc ctaccgtacc tcgcattacc cttacgctga agagatgctc gactgggcag | 4800 |
| atgaacatgg catcgtggtg attgatgaaa ctgctgctgt cggctttaac ctctctttag | 4860 |
| gcattggttt cgaagcgggc aacaagccga agaactgta cagcgaagag cagtcaacg | 4920 |
| gggaaactca gcaagcgcac ttacaggcga ttaaagagct gatagcgcgt gacaaaaacc | 4980 |
| acccaagcgt ggtgatgtgg agtattgcca acgaaccgga tacccgtcct gcacgggaat | 5040 |
| atttcggcat tcgccactg gcggaagcaa cgcgtaaact cgacccgacg cgtccgatca | 5100 |
| cctgcgtcaa tgtaatgttc tgcgacgctc acaccgatac catcagcgat ctctttgatg | 5160 |
| tgctgtgcct gaaccgttat tacggatggt atgtccaaag cggcgatttg aaacggcag | 5220 |
| agaaggtact ggaaaaagaa cttctggcct ggcaggagaa actgcatcag ccgattatca | 5280 |
| tcaccgaata cggcgtggat acgttagccg gctgcactc aatgtacacc gacatgtgga | 5340 |
| gtgaagagta tcagtgtgca tggctggata tgtatcaccg cgtctttgat cgcgtcagcg | 5400 |
| ccgtcgtcgg tgaacaggta tggaatttcg ccgattttgc gacctcgcaa ggcatattgc | 5460 |
| gcgttggcgg taacaagaaa gggatcttca ctcgcgaccg caaaccgaag tcggcggctt | 5520 |

```
ttctgctgca aaaacgctgg actggcatga acttcggtga aaaaccgcag cagggaggca    5580
aacaatgaat caacaactct cctggcgcac catcgtcggc tacagcctcg gtggggaatt    5640
cgagctcgcc cggggatcct ctagctagag ctttcgttcg tatcatcggt ttcgacaacg    5700
ttcgtcaagt tcaatgcatc agtttcattg cgcacacacc agaatcctac tgagttcgag    5760
tattatggca ttgggaaaac tgttttttctt gtaccatttg ttgtgcttgt aatttactgt    5820
gttttttatt cggttttcgc tatcgaactg tgaaatggaa atggatggag aagagttaat    5880
gaatgatatg gtccttttgt tcattctcaa attaatatta tttgttttt ctcttatttg    5940 ttgtgtgttg aatttgaaat tataagagat atgcaaacat tttgttttga gtaaaaatgt    6000
gtcaaatcgt ggcctctaat gaccgaagtt aatatgagga gtaaaacact tgtagttgta    6060
ccattatgct tattcactag gcaacaaata tattttcaga cctagaaaag ctgcaaatgt    6120
tactgaatac aagtatgtcc tcttgtgttt tagacattta tgaactttcc tttatgtaat    6180
tttccagaat ccttgtcaga ttctaatcat tgctttataa ttatagttat actcatggat    6240
ttgtagttga gtatgaaaat attttttaat gcattttatg acttgccaat tgattgacaa    6300
catgcatcaa tcgacctgca gcccaagctt gagctcagga tttagcagca ttccagattg    6360
ggttcaatca acaaggtacg agccatatca ctttattcaa attggtatcg ccaaaaccaa    6420
gaaggaactc ccatcctcaa aggtttgtaa ggaagaattc tcagtccaaa gcctcaacaa    6480
ggtcagggta cagagtctcc aaaccattag ccaaaagcta caggagatca atgaagaatc    6540
ttcaatcaaa gtaaactact gttccagcac atgcatcatg gtcagtaagt ttcagaaaaa    6600
gacatccacc gaagacttaa agttagtggg catctttgaa agtaatcttg tcaacatcga    6660
gcagctggct tgtggggacc agacaaaaaa ggaatggtgc agaattgtta ggcgcaccta    6720
ccaaaagcat ctttgccttt attgcaaaga taaagcagat tcctctagta caagtgggga    6780
acaaaataac gtggaaaaga gctgtcctga cagcccactc actaatgcgt atgacgaacg    6840
cagtgacgac cacaaaagaa ttccctctat ataagaaggc attcattccc atttgaagga    6900
tcatcagata ctgaaccaat ccttctagaa gatctccaca atggcttcct ctatgctctc    6960
ttccgctact atggttgcct ctccggctca ggccactatg gtcgctcctt caacggact    7020 taagtcctcc gctgccttcc cagccacccg caaggctaac aacgacatta cttccatcac    7080
aagcaacggc ggaagagtta actgcatgca ggtgtggcct ccgattggaa agaagaagtt    7140
tgagactctc tcttaccttc ctgaccttac cgattccggt ggtcgcgtca actgcatgca    7200
ggccatggct gagaaccaca agaaggttgg tatcgctgga gctggaatcg ttggtgtttg    7260
cactgctttg atgcttcaac gtcgtggatt caaggttacc ttgattgatc caaacccacc    7320
aggtgaaggt gcttctttcg gtaacgctgg ttgcttcaac ggttcctccg ttgttccaat    7380
gtccatgcca ggaaacttga ctagcgttcc aaagtggctt cttgacccaa tgggtccatt    7440
gtccatccgt ttcagctact tccaaccat catgccttgg ttgattcgtt tcttgcttgc    7500
tggaagacca aacaaggtga aggagcaagc taaggcactc cgtaacctca tcaagtccac    7560
tgtgcctttg atcaagtcct ggctgaggga ggctgatgct agccacctta tccgtcacga    7620
aggtcacctt accgtgtacc gtggagaagc agacttcgcc aaggaccgtg gaggttggga    7680
acttcgtcgt ctcaacggtg ttcgtactca aatcctcagc gctgatgcat tgcgtgattt    7740
cgatcctaac ttgtctcacg cctttaccaa gggaatcctt atcgaagaga acggtcacac    7800
catcaaccca caaggtctcg tgactctctt gtttcgtcgt ttcatcgcta acggtggaga    7860
```

-continued

| | |
|---|---|
| gttcgtgtct gctcgtgtta tcggattcga gactgaaggt cgtgctctca agggtatcac | 7920 |
| caccaccaac ggtgttcttg ctgttgatgc agctgttgtt gcagctggtg cacactccaa | 7980 |
| gtctcttgct aactcccttg gtgatgacat cccattggat accgaacgtg gataccacat | 8040 |
| cgtgatcgcc aacccagaag ctgctccacg tattccaact accgatgctt ctggaaagtt | 8100 |
| ccggtccaaa tttgtttaca ttgtgtccaa atttcggctg atttggactt ccctagctat | 8160 |
| gccaactaag ctaataaaaa acatgaaaca acaattacaa actgtcgagc acaccttcta | 8220 |
| caaactagct tagatttcta ttggaagtta caaaacagta aaactaccaa taggatacta | 8280 |
| aattaaacat attaaactat tactcctcaa aagcttgtac aatttgcaga agaaatgatg | 8340 |
| gttgcccaaa agcttcaaag ggaacctgct gggaagcctg ctgggacgct ggggatgctg | 8400 |
| gcagcagcat accttggctt gaagtactct tctctcattg gttttgcttc ccttgcccat | 8460 |
| gtggtcttca tatggcctca ttacttccca agggcttcaa atcagtaggt ggtggcaacc | 8520 |
| aaaagcatca aaaacatctc ctaaaactag cttatacaac cggattacat gagcttatac | 8580 |
| tagcttaact cttaaagcat gattaacata atgatgttta aggtgtcatt aagtattact | 8640 |
| aatcttgctt aagtagagat taacatagga ttagcctaat caagttgctt aagtaaggtt | 8700 |
| ttagaataaa ccgagctagt taggcttaag tagagattaa cataggatta gcctaatcaa | 8760 |
| gttgcttaag taaggtttta gaataaaccg agctagtt | 8798 |

<210> SEQ ID NO 5
<211> LENGTH: 8418
<212> TYPE: DNA
<213> ORGANISM: Sugar beet

<400> SEQUENCE: 5

| | |
|---|---|
| aagcttgagc tcaggattta gcagcattcc agattgggtt caatcaacaa ggtacgagcc | 60 |
| atatcacttt attcaaattg gtatcgccaa aaccaagaag gaactcccat cctcaaaggt | 120 |
| ttgtaaggaa gaattctcag tccaaagcct caacaaggtc agggtacaga gtctccaaac | 180 |
| cattagccaa aagctacagg agatcaatga agaatcttca atcaaagtaa actactgttc | 240 |
| cagcacatgc atcatggtca gtaagtttca gaaaagaca tccaccgaag acttaaagtt | 300 |
| agtgggcatc tttgaaagta atcttgtcaa catcgagcag ctggcttgtg gggaccagac | 360 |
| aaaaaaggaa tggtgcagaa ttgttaggcg cacctaccaa aagcatcttt gcctttattg | 420 |
| caaagataaa gcagattcct ctagtacaag tggggaacaa aataacgtgg aaaagagctg | 480 |
| tcctgacagc ccactcacta atgcgtatga cgaacgcagt gacgaccaca aaagaattcc | 540 |
| ctctatataa gaaggcattc attcccattt gaaggatcat cagatactga accaatcctt | 600 |
| ctagaagatc taagcttatc gataagcttg atgtaattgg aggaagatca aaattttcaa | 660 |
| tccccattct tcgattgctt caattgaagt ttctccgatg gcgcaagtta gcagaatctg | 720 |
| caatggtgtg cagaacccat ctcttatctc caatctctcg aaatccagtc aacgcaaatc | 780 |
| tcccttatcg gtttctctga agacgcagca gcatccacga gcttatccga tttcgtcgtc | 840 |
| gtggggattg aagaagagtg ggatgacgtt aattggctct gagcttcgtc ctcttaaggt | 900 |
| catgtcttct gtttccacgg cgtgcatgct tcacggtgca agcagccgtc cagcaactgc | 960 |
| tcgtaagtcc tctggtcttt ctggaaccgt ccgtattcca ggtgacaagt ctatctccca | 1020 |
| caggtccttc atgtttggag gtctcgctag cggtgaaact cgtatcaccg gtctttggga | 1080 |
| aggtgaagat gttatcaaca ctggtaaggc tatgcaagct atgggtgcca gaatccgtaa | 1140 |
| ggaaggtgat acttggatca ttgatggtgt tggtaacggt ggactccttg ctcctgaggc | 1200 |

-continued

```
tcctctcgat ttcggtaacg ctgcaactgg ttgccgtttg actatgggtc ttgttggtgt   1260
ttacgatttc gatagcactt tcattggtga cgcttctctc actaagcgtc caatgggtcg   1320
tgtgttgaac ccacttcgcg aaatgggtgt gcaggtgaag tctgaagacg gtgatcgtct   1380
tccagttacc ttgcgtggac caaagactcc aacgccaatc acctacaggg tacctatggc   1440
ttccgctcaa gtgaagtccg ctgttctgct tgctggtctc aacaccccag gtatcaccac   1500
tgttatcgag ccaatcatga ctcgtgacca cactgaaaag atgcttcaag gttttggtgc   1560
taaccttacc gttgagactg atgctgacgg tgtgcgtacc atccgtcttg aaggtcgtgg   1620
taagctcacc ggtcaagtga ttgatgttcc aggtgatcca tcctctactg ctttcccatt   1680
ggttgctgcc ttgcttgttc caggttccga cgtcaccatc cttaacgttt tgatgaaccc   1740
aacccgtact ggtctcatct tgactctgca ggaaatgggt gccgacatcg aagtgatcaa   1800
cccacgtctt gctggtggag aagacgtggc tgacttgcgt gttcgttctt ctactttgaa   1860
gggtgttact gttccagaag accgtgctcc ttctatgatc gacgagtatc caattctcgc   1920
tgttgcagct gcattcgctg aaggtgctac cgttatgaac ggtttggaag aactccgtgt   1980
taaggaaagc gaccgtcttt ctgctgtcgc aaacggtctc aagctcaacg gtgttgattg   2040
cgatgaaggt gagacttctc tcgtcgtgcg tggtcgtcct gacggtaagg gtctcggtaa   2100
cgcttctgga gcagctgtcg ctacccacct cgatcaccgt atcgctatga gcttcctcgt   2160
tatgggtctc gtttctgaaa accctgttac tgttgatgat gctactatga tcgctactag   2220
cttcccagag ttcatggatt tgatggctgg tcttggagct aagatcgaac tctccgacac   2280
taaggctgct tgatgagctc aagaattcga gctcggtacc ggatcctcta gctagagctt   2340
tcgttcgtat catcggtttc gacaacgttc gtcaagttca atgcatcagt ttcattgcgc   2400
acacaccaga atcctactga gttcgagtat tatggcattg ggaaaactgt ttttcttgta   2460
ccatttgttg tgcttgtaat ttactgtgtt ttttattcgg ttttcgctat cgaactgtga   2520
aatggaaatg gatggagaag agttaatgaa tgatatggtc cttttgttca ttctcaaatt   2580
aatattattt gttttttctc ttatttgttg tgtgttgaat ttgaaattat aagagatatg   2640
caaacatttt gttttgagta aaaatgtgtc aaatcgtggc ctctaatgac cgaagttaat   2700
atgaggagta aaacacttgt agttgtacca ttatgcttat tcactaggca acaaatatat   2760
tttcagacct agaaaagctg caaatgttac tgaatacaag tatgtcctct tgtgttttag   2820
acatttatga actttccttt atgtaatttt ccagaatcct tgtcagattc taatcattgc   2880
tttataatta tagttatact catggatttg tagttgagta tgaaaatatt ttttaatgca   2940
ttttatgact tgccaattga ttgacaacat gcatcaatcg acctgcagcc actcgaagcg   3000
gccgcgttca agcttctgca ggtccgatgt gagacttttc aacaaagggt aatatccgga   3060
aacctcctcg gattccattg cccagctatc tgtcacttta ttgtgaagat agtggaaaag   3120
gaaggtggct cctacaaatg ccatcattgc gataaggaa aggccatcgt gaagatgcc   3180 tctgccgaca gtggtcccaa agatggaccc cacccacga ggagcatcgt ggaaaaagaa   3240
gacgttccaa ccacgtcttc aaagcaagtg gattgatgtg atggtccgat gtgagacttt   3300
tcaacaaagg gtaatatccg gaaacctcct cggattccat gcccagcta tctgtcactt   3360 tattgtgaag atagtggaaa aggaaggtgg ctcctacaaa tgccatcatt gcgataaagg   3420
aaaggccatc gttgaagatg cctctgccga cagtggtccc aaagatggac ccccacccac   3480
gaggagcatc gtggaaaaag aagacgttcc aaccacgtct tcaaagcaag tggattgatg   3540
```

-continued

```
tgatatctcc actgacgtaa gggatgacgc acaatcccac tatccttcgc aagacccttc   3600
ctctatataa ggaagttcat ttcatttgga gaggacacgc tgacaagctg actctagcag   3660
atctccatgg tccgtcctgt agaaacccca acccgtgaaa tcaaaaaact cgacggcctg   3720
tgggcattca gtctggatcg cgaaaactgt ggaattgatc agcgttggtg ggaaagcgcg   3780
ttacaagaaa gccgggcaat tgctgtgcca ggcagttttta acgatcagtt cgccgatgca   3840
gatattcgta attatgcggg caacgtctgg tatcagcgcg aagtctttat accgaaaggt   3900
tgggcaggcc agcgtatcgt gctgcgtttc gatgcggtca ctcattacgg caaagtgtgg   3960
gtcaataatc aggaagtgat ggagcatcag gcggcctata cgccatttga agccgatgtc   4020
acgccgtatg ttattgccgg aaaagtgta cgtatcaccg tttgtgtgaa caacgaactg   4080
aactggcaga ctatcccgcc gggaatggtg attaccgacg aaaacggcaa gaaaaagcag   4140
tcttacttcc atgatttctt taactatgcc ggaatccatc gcagcgtaat gctctacacc   4200
acgccgaaca cctgggtgga cgatatcacc gtggtgacgc atgtcgcgca agactgtaac   4260
cacgcgtctg ttgactggca ggtggtggcc aatggtgatg tcagcgttga actgcgtgat   4320
gcggatcaac aggtggttgc aactggacaa ggcactagcg ggactttgca agtggtgaat   4380
ccgcacctct ggcaaccggg tgaaggttat ctctatgaac tgtgcgtcac agccaaaagc   4440
cagacagagt gtgatatcta cccgcttcgc gtcggcatcc ggtcagtggc agtgaagggc   4500
gaacagttcc tgattaacca caaaccgttc tactttactg gctttggtcg tcatgaagat   4560
gcggacttac gtggcaaagg attcgataac gtgctgatgg tgcacgacca cgcattaatg   4620
gactggattg gggccaactc ctaccgtacc tcgcattacc cttacgctga agagatgctc   4680
gactgggcag atgaacatgg catcgtggtg attgatgaaa ctgctgctgt cggctttaac   4740
ctctctttag gcattggttt cgaagcgggc aacaagccga agaactgta cagcgaagag   4800
gcagtcaacg gggaaactca gcaagcgcac ttacaggcga ttaaagagct gatagcgcgt   4860
gacaaaaacc acccaagcgt ggtgatgtgg agtattgcca acgaaccgga tacccgtcct   4920
gcacgggaat atttcggcat ttcgccactg gcggaagcaa cgcgtaaact cgacccgacg   4980
cgtccgatca cctgcgtcaa tgtaatgttc tgcgacgctc acaccgatac catcagcgat   5040
ctctttgatg tgctgtgcct gaaccgttat tacggatggt atgtccaaag cggcgatttg   5100
gaaacggcag agaaggtact ggaaaaagaa cttctggcct ggcaggagaa actgcatcag   5160
ccgattatca tcaccgaata cggcgtggat acgttagccg ggctgcactc aatgtacacc   5220
gacatgtgga gtgaagagta tcagtgtgca tggctggata tgtatcaccg cgtctttgat   5280
cgcgtcagcg ccgtcgtcgg tgaacaggta tggaatttcg ccgattttgc gacctcgcaa   5340
ggcatattgc gcgttggcgg taacaagaaa gggatcttca ctcgcgaccg caaaccgaag   5400
tcggcggctt ttctgctgca aaaacgctgg actggcatga acttcggtga aaaaccgcag   5460
cagggaggca aacaatgaat caacaactct cctggcgcac catcgtcggc tacagcctcg   5520
gtggggaatt cgagctcgcc cggggatcct ctagctagag ctttcgttcg tatcatcggt   5580
ttcgacaacg ttcgtcaagt tcaatgcatc agtttcattg cgcacacacc agaatcctac   5640
tgagttcgag tattatggca ttgggaaaac tgttttttctt gtaccatttg ttgtgcttgt   5700
aatttactgt gttttttatt cggttttcgc tatcgaactg tgaaatggaa atggatggag   5760
aagagttaat gaatgatatg gtcctttttgt tcattctcaa attaatatta tttgttttttt   5820
ctcttatttg ttgtgtgttg aatttgaaat tataagagat atgcaaacat tttgttttga   5880
gtaaaaatgt gtcaaatcgt ggcctctaat gaccgaagtt aatatgagga gtaaaacact   5940
```

-continued

```
tgtagttgta ccattatgct tattcactag gcaacaaata tattttcaga cctagaaaag    6000
ctgcaaatgt tactgaatac aagtatgtcc tcttgtgttt tagacattta tgaacttttcc   6060
tttatgtaat tttccagaat ccttgtcaga ttctaatcat tgctttataa ttatagttat    6120
actcatggat ttgtagttga gtatgaaaat atttttttaat gcattttatg acttgccaat   6180
tgattgacaa catgcatcaa tcgacctgca gcccaagctt gagctcagga tttagcagca    6240
ttccagattg ggttcaatca acaaggtacg agccatatca ctttattcaa attggtatcg    6300
ccaaaaccaa gaaggaactc ccatcctcaa aggtttgtaa ggaagaattc tcagtccaaa    6360
gcctcaacaa ggtcagggta cagagtctcc aaaccattag ccaaaagcta caggagatca    6420
atgaagaatc ttcaatcaaa gtaaactact gttccagcac atgcatcatg gtcagtaagt    6480
ttcagaaaaa gacatccacc gaagacttaa agttagtggg catctttgaa agtaatcttg    6540
tcaacatcga gcagctggct tgtggggacc agacaaaaaa ggaatggtgc agaattgtta    6600
ggcgcaccta ccaaaagcat ctttgccttt attgcaaaga taaagcagat tcctctagta    6660
caagtgggga acaaaataac gtggaaaaga gctgtcctga cagcccactc actaatgcgt    6720
atgacgaacg cagtgacgac cacaaaagaa ttccctctat ataagaaggc attcattccc    6780
atttgaagga tcatcagata ctgaaccaat ccttctagaa gatctccaca atggcttcct    6840
ctatgctctc ttccgctact atggttgcct ctccggctca ggccactatg gtcgctcctt    6900
tcaacggact taagtcctcc gctgccttcc cagccacccg caaggctaac aacgacatta    6960
cttccatcac aagcaacggc ggaagagtta actgcatgca ggtgtggcct ccgattggaa    7020
agaagaagtt tgagactctc tcttaccttc ctgaccttac cgattccggt ggtcgcgtca    7080
actgcatgca ggccatggct gagaaccaca agaaggttgg tatcgctgga gctggaatcg    7140
ttggtgtttg cactgctttg atgcttcaac gtcgtggatt caaggttacc ttgattgatc    7200
caaacccacc aggtgaaggt gcttctttcg gtaacgctgg ttgcttcaac ggttcctccg    7260
ttgttccaat gtccatgcca ggaaacttga ctagcgttcc aaagtggctt cttgacccaa    7320
tgggtccatt gtccatccgt ttcagctact ttccaaccat catgccttgg ttgattcgtt    7380
tcttgcttgc tggaagacca acaaggtgaa ggagcaagc taaggcactc cgtaacctca    7440
tcaagtccac tgtgcctttg atcaagtcct ggctgaggaa ggctgatgct agccacctta    7500
tccgtcacga aggtcacctt accgtgtacc gtggagaagc agacttcgcc aaggaccgtg    7560
gaggttggga acttcgtcgt ctcaacggtg ttcgtactca aatcctcagc gctgatgcat    7620
tgcgtgattt cgatcctaac ttgtctcacg cctttaccaa gggaatcctt atcgaagaga    7680
acggtcacac catcaaccca caaggtctcg tgactctctt gtttcgtcgt ttcatcgcta    7740
acggtggaga gttcgtgtct gctcgtgtta tcggattcga gactgaaggt cgtgctctca    7800
agggtatcac caccaccaac ggtgttcttg ctgttgatgc agctgttgtt gcagctggtg    7860
cacactccaa gtctcttgct aactcccttg gtgatgacat cccattggat accgaacgtg    7920
gataccacat cgtgatcgcc aacccagaag ctgctccacg tattccaact accgatgctt    7980
ctggaaagtt catcgctact cctatggaga tgggtcttcg tgttgctgga accgttgagt    8040
tcgctggtct cactgctgct cctaactgga agcgtgctca cgttctctac actcacgctc    8100
gtaagttgct tccagctctc gctcctgcca gttctgaaga acgttactcc aagtggatgg    8160
gtttccgtcc aagcatccca gattcccttc agtgattgg tcgtgctacc cgtactccag    8220
acgttatcta cgctttcggt cacggtcacc tcggtatgac tggtgctcca atgaccgcaa    8280
```

```
ccctcgtttc tgagctcctc gcaggtgaga agacctctat cgacatctct ccattcgcac    8340
caaaccgttt cggtattggt aagtccaagc aaactggtcc tgcatcctaa gtgggaattc    8400
gagctcggta ccggatcc                                                   8418
```

<210> SEQ ID NO 6
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 6

```
caccggtctt ttggaaggtg aag                                               23
```

<210> SEQ ID NO 7
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 7

```
aacgagaccc ataacgagga agc                                               23
```

<210> SEQ ID NO 8
<211> LENGTH: 23
<212> TYPE: DNA
<213> ORGANISM: Articifial sequence
<220> FEATURE:
<221> NAME/KEY: misc_feature
<222> LOCATION: (1)..(23)
<223> OTHER INFORMATION: Primer

<400> SEQUENCE: 8

```
aaacagtccc gtgcatcccc aac                                               23
```

<210> SEQ ID NO 9
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Pimer

<400> SEQUENCE: 9

```
gacgctctcc ttgattctgt ccc                                               23
```

<210> SEQ ID NO 10
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer

<400> SEQUENCE: 10

```
caagaaggtt ggtatcgctg                                                   20
```

<210> SEQ ID NO 11
<211> LENGTH: 23

```
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 11
tcttttgtgg tcgtcactgc gtt                                        23

<210> SEQ ID NO 12
<211> LENGTH: 24
<212> TYPE: DNA
<213> ORGANISM: Artificial sequence
<220> FEATURE:
<221> NAME/KEY: misc_feature
<222> LOCATION: (1)..(24)
<223> OTHER INFORMATION: Primer

<400> SEQUENCE: 12
gcgagctcta atacgactca ctat                                       24

<210> SEQ ID NO 13
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 13
cgcgagctca attaaccctc act                                        23

<210> SEQ ID NO 14
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer

<400> SEQUENCE: 14
tctgtaccct gaccttgttg                                            20

<210> SEQ ID NO 15
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer

<400> SEQUENCE: 15
cgtggatacc acatcgtgat                                            20

<210> SEQ ID NO 16
<211> LENGTH: 19
<212> TYPE: DNA
<213> ORGANISM: Artificial sequence
<220> FEATURE:
<221> NAME/KEY: misc_feature
<222> LOCATION: (1)..(19)
<223> OTHER INFORMATION: Primer

<400> SEQUENCE: 16
```

-continued

```
accttggctt gaagtactc                                              19

<210> SEQ ID NO 17
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 17
tcaacctaca gctgatttgg acc                                         23

<210> SEQ ID NO 18
<211> LENGTH: 22
<212> TYPE: DNA
<213> ORGANISM: Artificial sequence
<220> FEATURE:
<221> NAME/KEY: misc_feature
<222> LOCATION: (1)..(22)
<223> OTHER INFORMATION: Primer

<400> SEQUENCE: 18
ggaccggaac gacaatctga tc                                          22

<210> SEQ ID NO 19
<211> LENGTH: 22
<212> TYPE: DNA
<213> ORGANISM: Artificial sequence
<220> FEATURE:
<221> NAME/KEY: misc_feature
<222> LOCATION: (1)..(22)
<223> OTHER INFORMATION: Primer

<400> SEQUENCE: 19
ctagggaagt ccaaatcagc cg                                          22

<210> SEQ ID NO 20
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 20
tttggaccgg aactttccag aag                                         23

<210> SEQ ID NO 21
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 21
ctaacttgcg ccatcggaga aac                                         23

<210> SEQ ID NO 22
<211> LENGTH: 23
<212> TYPE: DNA
<213> ORGANISM: Artificial sequence
<220> FEATURE:
<221> NAME/KEY: misc_feature
```

<222> LOCATION: (1)..(23)
<223> OTHER INFORMATION: Primer

<400> SEQUENCE: 22
gacttgtcac ctggaatacg gac                                             23

<210> SEQ ID NO 23
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 23
attcttgagc tcatcaagca gcc                                             23

<210> SEQ ID NO 24
<211> LENGTH: 22
<212> TYPE: DNA
<213> ORGANISM: Artificial sequence
<220> FEATURE:
<221> NAME/KEY: misc_feature
<222> LOCATION: (1)..(22)
<223> OTHER INFORMATION: Primer

<400> SEQUENCE: 24
aaggttggta tcgctggagc tg                                              22

<210> SEQ ID NO 25
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: Primer

<400> SEQUENCE: 25
tctccacaat ggcttcctct atg                                             23

<210> SEQ ID NO 26
<211> LENGTH: 671
<212> TYPE: DNA
<213> ORGANISM: Artificial sequence
<220> FEATURE:
<221> NAME/KEY: misc_feature
<222> LOCATION: (1)..(671)
<223> OTHER INFORMATION: Probe

<400> SEQUENCE: 26
caagatggat tgcacgcagg ttctccggcc gcttgggtgg agaggctatt cggctatgac     60
tgggcacaac agacaatcgg ctgctctgat gccgccgtgt tccggctgtc agcgcagggg    120
cgcccggttc tttttgtcaa gaccgacctg tccggtgccc tgaatgaact gcaggacgag    180
gcagcgcggc tatcgtggct ggccacgacg ggcgttcctt gcgcagctgt gctcgacgtt    240
gtcactgaag cgggaaggga ctggctgcta ttgggcgaag tgccggggca ggatctcctg    300
tcatctcacc ttgctcctgc cgagaaagta tccatcatgg ctgatgcaat gcggcggctg    360
catacgcttg atccggctac ctgcccattc gaccaccaag cgaaacatcg catcgagcga    420
gcacgtactc ggatggaagc cggtcttgtc gatcaggatg atctggacga agagcatcag    480
gggctcgcgc cagccgaact gttcgccagg ctcaaggcgc gcatgcccga cggcgaggat    540

```
ctcgtcgtga cccatggcga tgcctgcttg ccgaatatca tggtggaaaa tggccgcttt        600
tctggattca tcgactgtgg ccggctgggt gtggcggacc gctatcagga catagcgttg        660
gctacccgtg a                                                            671

<210> SEQ ID NO 27
<211> LENGTH: 739
<212> TYPE: DNA
<213> ORGANISM: Artificial sequence
<220> FEATURE:
<221> NAME/KEY: misc_feature
<222> LOCATION: (1)..(739)
<223> OTHER INFORMATION: Amplified fragment

<400> SEQUENCE: 27
ggaccggaac gacaatctga tccccatcaa gcttgagctc aggatttagc agcattccag         60
attgggttca atcaacaagg tacgagccat atcactttat tcaaattggt atcgccaaaa        120
ccaagaagga actcccatcc tcaaaggttt gtaaggaaga attctcagtc caaagcctca        180
acaaggtcag ggtacagagt ctccaaacca ttagccaaaa gctacaggag atcaatgaag        240
aatcttcaat caaagtaaac tactgttcca gcacatgcat catggtcagt aagtttcaga        300
aaaagacatc caccgaagac ttaaagttag tgggcatctt tgaaagtaat cttgtcaaca        360
tcgagcagct ggcttgtggg gaccagacaa aaaggaatg gtgcagaatt gttaggcgca        420
cctaccaaaa gcatctttgc ctttattgca aagataaagc agattcctct agtacaagtg        480
gggaacaaaa taacgtggaa aagagctgtc ctgacagccc actcactaat gcgtatgacg        540
aacgcagtga cgaccacaaa gaattccct ctatataaga aggcattcat tcccatttga        600
aggatcatca gatactgaac caatccttct agaagatcta agcttatcga taagcttgat        660
gtaattggag gaagatcaaa attttcaatc cccattcttc gattgcttca attgaagttt        720
ctccgatggc gcaagttag                                                    739

<210> SEQ ID NO 28
<211> LENGTH: 757
<212> TYPE: DNA
<213> ORGANISM: Artificial sequence
<220> FEATURE:
<221> NAME/KEY: misc_feature
<222> LOCATION: (1)..(757)
<223> OTHER INFORMATION: Amplified fragment

<400> SEQUENCE: 28
tcaacctaca gctgatttgg accggaacga caatctgatc cccatcaagc ttgagctcag         60
gatttagcag cattccagat tgggttcaat caacaaggta cgagccatat cactttattc        120
aaattggtat cgccaaaacc aagaaggaac tcccatcctc aaaggtttgt aaggaagaat        180
tctcagtcca aagcctcaac aaggtcaggg tacagagtct ccaaaccatt agccaaaagc        240
tacaggagat caatgaagaa tcttcaatca agtaaacta ctgttccagc acatgcatca        300
tggtcagtaa gtttcagaaa aagacatcca ccgaagactt aaagttagtg ggcatctttg        360
aaagtaatct tgtcaacatc gagcagctgg cttgtgggga ccagacaaaa aggaatggt        420 gcagaattgt taggcgcacc taccaaaagc atctttgcct ttattgcaaa gataaagcag        480
attcctctag tacaagtggg gaacaaaata cgtggaaaa gagctgtcct gacagcccac        540
tcactaatgc gtatgacgaa cgcagtgacg accacaaaag aattccctct atataagaag        600
gcattcattc ccatttgaag gatcatcaga tactgaacca atccttctag aagatctaag        660
cttatcgata agcttgatgt aattggagga agatcaaaat tttcaatccc cattcttcga        720
```

```
ttgcttcaat tgaagtttct ccgatggcgc aagttag                            757
```

<210> SEQ ID NO 29
<211> LENGTH: 1057
<212> TYPE: DNA
<213> ORGANISM: Artificial sequence
<220> FEATURE:
<221> NAME/KEY: misc_feature
<222> LOCATION: (1)..(1057)
<223> OTHER INFORMATION: Amplified fragment

<400> SEQUENCE: 29

```
tcaacctaca gctgatttgg accggaacga caatctgatc cccatcaagc ttgagctcag     60
gatttagcag cattccagat tgggttcaat caacaaggta cgagccatat cactttattc    120
aaattggtat cgccaaaacc aagaaggaac tcccatcctc aaaggtttgt aaggaagaat    180
tctcagtcca aagcctcaac aaggtcaggg tacagagtct ccaaaccatt agccaaaagc    240
tacaggagat caatgaagaa tcttcaatca agtaaacta ctgttccagc acatgcatca     300
tggtcagtaa gtttcagaaa aagacatcca ccgaagactt aaagttagtg ggcatctttg    360
aaagtaatct tgtcaacatc gagcagctgg cttgtgggga ccagacaaaa aaggaatggt    420
gcagaattgt taggcgcacc taccaaaagc atctttgcct ttattgcaaa gataaagcag    480
attcctctag tacaagtggg gaacaaaata acgtggaaaa gagctgtcct gacagcccac    540
tcactaatgc gtatgacgaa cgcagtgacg accacaaaag aattccctct atataagaag    600
gcattcattc ccatttgaag gatcatcaga tactgaacca atccttctag aagatctaag    660
cttatcgata agcttgatgt aattggagga agatcaaaat tttcaatccc cattcttcga    720
ttgcttcaat tgaagtttct ccgatggcgc aagttagcag aatctgcaat ggtgtgcaga    780
acccatctct tatctccaat ctctcgaaat ccagtcaacg caaatctccc ttatcggttt    840
ctctgaagac gcagcagcat ccacgagctt atccgatttc gtcgtcgtgg ggattgaaga    900
agagtgggat gacgttaatt ggctctgagc ttcgtcctct taaggtcatg tcttctgttt    960
ccacggcgtg catgcttcac ggtgcaagca gccgtccagc aactgctcgt aagtcctctg   1020
gtctttctgg aaccgtccgt attccaggtg acaagtc                            1057
```

<210> SEQ ID NO 30
<211> LENGTH: 2352
<212> TYPE: DNA
<213> ORGANISM: Artificial sequence
<220> FEATURE:
<221> NAME/KEY: misc_feature
<222> LOCATION: (1)..(2352)
<223> OTHER INFORMATION: Amplified fragment

<400> SEQUENCE: 30

```
tcaacctaca gctgatttgg accggaacga caatctgatc cccatcaagc ttgagctcag     60
gatttagcag cattccagat tgggttcaat caacaaggta cgagccatat cactttattc    120
aaattggtat cgccaaaacc aagaaggaac tcccatcctc aaaggtttgt aaggaagaat    180
tctcagtcca aagcctcaac aaggtcaggg tacagagtct ccaaaccatt agccaaaagc    240
tacaggagat caatgaagaa tcttcaatca agtaaacta ctgttccagc acatgcatca     300
tggtcagtaa gtttcagaaa aagacatcca ccgaagactt aaagttagtg ggcatctttg    360
aaagtaatct tgtcaacatc gagcagctgg cttgtgggga ccagacaaaa aaggaatggt    420
gcagaattgt taggcgcacc taccaaaagc atctttgcct ttattgcaaa gataaagcag    480
```

```
attcctctag tacaagtggg gaacaaaata acgtggaaaa gagctgtcct gacagcccac      540
tcactaatgc gtatgacgaa cgcagtgacg accacaaaag aattccctct atataagaag      600
gcattcattc ccatttgaag gatcatcaga tactgaacca atccttctag aagatctaag      660
cttatcgata agcttgatgt aattggagga agatcaaaat tttcaatccc cattcttcga      720
ttgcttcaat tgaagtttct ccgatggcgc aagttagcag aatctgcaat ggtgtgcaga      780
acccatctct tatctccaat ctctcgaaat ccagtcaacg caaatctccc ttatcggttt      840
ctctgaagac gcagcagcat ccacgagctt atccgatttc gtcgtcgtgg ggattgaaga      900
agagtgggat gacgttaatt ggctctgagc ttcgtcctct aaggtcatg tcttctgttt        960 ccacggcgtg catgcttcac ggtgcaagca gccgtccagc aactgctcgt aagtcctctg      1020
gtctttctgg aaccgtccgt attccaggtg acaagtctat ctcccacagg tccttcatgt      1080
ttggaggtct cgctagcggt gaaactcgta tcaccggtct tttggaaggt gaagatgtta      1140
tcaacactgg taaggctatg caagctatgg gtgccagaat ccgtaaggaa ggtgatactt      1200
ggatcattga tggtgttggt aacgtggac tccttgctcc tgaggctcct ctcgatttcg       1260
gtaacgctgc aactggttgc cgtttgacta tgggtcttgt tggtgtttac gatttcgata      1320
gcactttcat tggtgacgct ctctcacta agcgtccaat gggtcgtgtg ttgaacccac        1380
ttcgcgaaat gggtgtgcag gtgaagtctg aagacggtga tcgtcttcca gttaccttgc      1440
gtggaccaaa gactccaacg ccaatcacct acagggtacc tatggcttcc gctcaagtga      1500
agtccgctgt tctgcttgct ggtctcaaca ccccaggtat caccactgtt atcgagccaa      1560
tcatgactcg tgaccacact gaaaagatgc ttcaaggttt tggtgctaac cttaccgttg      1620
agactgatgc tgacggtgtg cgtaccatcc gtcttgaagg tcgtggtaag ctcaccggtc      1680
aagtgattga tgttccaggt gatccatcct ctactgcttt cccattggtt gctgccttgc      1740
ttgttccagg ttccgacgtc accatcctta acgttttgat gaacccaacc cgtactggtc      1800
tcatcttgac tctgcaggaa atgggtgccg acatcgaagt gatcaaccca cgtcttgctg      1860
gtggagaaga cgtggctgac ttgcgtgttc gttcttctac tttgaagggt gttactgttc      1920
cagaagaccg tgctccttct atgatcgacg agtatccaat tctcgctgtt gcagctgcat      1980
tcgctgaagg tgctaccgtt atgaacggtt tggaagaact ccgtgttaag gaaagcgacc      2040
gtctttctgc tgtcgcaaac ggtctcaagc tcaacggtgt tgattgcgat gaaggtgaga      2100
cttctctcgt cgtgcgtggt cgtcctgacg gtaagggtct cggtaacgct tctggagcag      2160
ctgtcgctac ccacctcgat caccgtatcg ctatgagctt cctcgttatg ggtctcgttt      2220
ctgaaaaccc tgttactgtt gatgatgcta ctatgatcgc tactagcttc ccagagttca      2280
tggatttgat ggctggtctt ggagctaaga tcgaactctc cgacactaag gctgcttgat      2340
gagctcaaga at                                                          2352
```

<210> SEQ ID NO 31
<211> LENGTH: 1039
<212> TYPE: DNA
<213> ORGANISM: Artificial sequence
<220> FEATURE:
<221> NAME/KEY: misc_feature
<222> LOCATION: (1)..(1039)
<223> OTHER INFORMATION: Amplified fragment

<400> SEQUENCE: 31

```
ggaccggaac gacaatctga tccccatcaa gcttgagctc aggatttagc agcattccag       60
attgggttca atcaacaagg tacgagccat atcactttat tcaaattggt atcgccaaaa      120
```

```
ccaagaagga actcccatcc tcaaaggttt gtaaggaaga attctcagtc caaagcctca        180
acaaggtcag ggtacagagt ctccaaacca ttagccaaaa gctacaggag atcaatgaag        240
aatcttcaat caaagtaaac tactgttcca gcacatgcat catggtcagt aagtttcaga        300
aaaagacatc caccgaagac ttaaagttag tgggcatctt tgaaagtaat cttgtcaaca        360
tcgagcagct ggcttgtggg gaccagacaa aaaggaatg gtgcagaatt gttaggcgca         420
cctaccaaaa gcatctttgc ctttattgca aagataaagc agattcctct agtacaagtg        480
gggaacaaaa taacgtggaa aagagctgtc ctgacagccc actcactaat gcgtatgacg        540
aacgcagtga cgaccacaaa agaattccct ctatataaga aggcattcat tcccatttga        600
aggatcatca gatactgaac caatccttct agaagatcta agcttatcga taagcttgat        660
gtaattggag gaagatcaaa attttcaatc cccattcttc gattgcttca attgaagttt        720
ctccgatggc gcaagttagc agaatctgca atggtgtgca gaacccatct cttatctcca        780
atctctcgaa atccagtcaa cgcaaatctc ccttatcggt ttctctgaag acgcagcagc        840
atccacgagc ttatccgatt tcgtcgtcgt ggggattgaa gaagagtggg atgacgttaa        900
ttggctctga gcttcgtcct cttaaggtca tgtcttctgt ttccacggcg tgcatgcttc        960
acggtgcaag cagccgtcca gcaactgctc gtaagtcctc tggtctttct ggaaccgtcc       1020
gtattccagg tgacaagtc                                                   1039
```

<210> SEQ ID NO 32
<211> LENGTH: 2334
<212> TYPE: DNA
<213> ORGANISM: Artificial sequence
<220> FEATURE:
<221> NAME/KEY: misc_feature
<222> LOCATION: (1)..(2334)
<223> OTHER INFORMATION: Amplified fragment

<400> SEQUENCE: 32

```
ggaccggaac gacaatctga tccccatcaa gcttgagctc aggatttagc agcattccag         60
attgggttca atcaacaagg tacgagccat atcactttat tcaaattggt atcgccaaaa        120
ccaagaagga actcccatcc tcaaaggttt gtaaggaaga attctcagtc caaagcctca        180
acaaggtcag ggtacagagt ctccaaacca ttagccaaaa gctacaggag atcaatgaag        240
aatcttcaat caaagtaaac tactgttcca gcacatgcat catggtcagt aagtttcaga        300
aaaagacatc caccgaagac ttaaagttag tgggcatctt tgaaagtaat cttgtcaaca        360
tcgagcagct ggcttgtggg gaccagacaa aaaggaatg gtgcagaatt gttaggcgca         420
cctaccaaaa gcatctttgc ctttattgca aagataaagc agattcctct agtacaagtg        480
gggaacaaaa taacgtggaa aagagctgtc ctgacagccc actcactaat gcgtatgacg        540
aacgcagtga cgaccacaaa agaattccct ctatataaga aggcattcat tcccatttga        600
aggatcatca gatactgaac caatccttct agaagatcta agcttatcga taagcttgat        660
gtaattggag gaagatcaaa attttcaatc cccattcttc gattgcttca attgaagttt        720
ctccgatggc gcaagttagc agaatctgca atggtgtgca gaacccatct cttatctcca        780
atctctcgaa atccagtcaa cgcaaatctc ccttatcggt ttctctgaag acgcagcagc        840
atccacgagc ttatccgatt tcgtcgtcgt ggggattgaa gaagagtggg atgacgttaa        900
ttggctctga gcttcgtcct cttaaggtca tgtcttctgt ttccacggcg tgcatgcttc        960
acggtgcaag cagccgtcca gcaactgctc gtaagtcctc tggtctttct ggaaccgtcc       1020
```

-continued

```
gtattccagg tgacaagtct atctcccaca ggtccttcat gtttggaggt ctcgctagcg    1080
gtgaaactcg tatcaccggt cttttggaag gtgaagatgt tatcaacact ggtaaggcta    1140
tgcaagctat gggtgccaga atccgtaagg aaggtgatac ttggatcatt gatggtgttg    1200
gtaacggtgg actccttgct cctgaggctc ctctcgattt cggtaacgct gcaactggtt    1260
gccgtttgac tatgggtctt gttggtgttt acgatttcga tagcactttc attggtgacg    1320
cttctctcac taagcgtcca atgggtcgtg tgttgaaccc acttcgcgaa atgggtgtgc    1380
aggtgaagtc tgaagacggt gatcgtcttc cagttacctt gcgtggacca aagactccaa    1440
cgccaatcac ctacagggta cctatggctt ccgctcaagt gaagtccgct gttctgcttg    1500
ctggtctcaa cacccaggt atcaccactg ttatcgagcc aatcatgact cgtgaccaca    1560
ctgaaaagat gcttcaaggt tttggtgcta accttaccgt tgagactgat gctgacggtg    1620
tgcgtaccat ccgtcttgaa ggtcgtggta agctcaccgg tcaagtgatt gatgttccag    1680
gtgatccatc ctctactgct ttcccattgg ttgctgcctt gcttgttcca ggttccgacg    1740
tcaccatcct taacgttttg atgaacccaa cccgtactgg tctcatcttg actctgcagg    1800
aaatgggtgc cgacatcgaa gtgatcaacc cacgtcttgc tggtggagaa gacgtggctg    1860
acttgcgtgt tcgttcttct actttgaagg gtgttactgt tccagaagac cgtgctcctt    1920
ctatgatcga cgagtatcca attctcgctg ttgcagctgc attcgctgaa ggtgctaccg    1980
ttatgaacgg tttggaagaa ctccgtgtta aggaaagcga ccgtctttct gctgtcgcaa    2040
acggtctcaa gctcaacggt gttgattgcg atgaaggtga gacttctctc gtcgtgcgtg    2100
gtcgtcctga cggtaagggt ctcggtaacg cttctggagc agctgtcgct acccacctcg    2160
atcaccgtat cgctatgagc ttcctcgtta tgggtctcgt ttctgaaaac cctgttactg    2220
ttgatgatgc tactatgatc gctactagct cccagagtt catggatttg atggctggtc    2280
ttggagctaa gatcgaactc tccgacacta aggctgcttg atgagctcaa gaat          2334
```

<210> SEQ ID NO 33
<211> LENGTH: 934
<212> TYPE: DNA
<213> ORGANISM: Artificial sequence
<220> FEATURE:
<221> NAME/KEY: misc_feature
<222> LOCATION: (1)..(934)
<223> OTHER INFORMATION: Amplified fragment

<400> SEQUENCE: 33

```
aaggttggta tcgctggagc tggaatcgtt ggtgtttgca ctgctttgat gcttcaacgt      60
cgtggattca aggttacctt gattgatcca aacccaccag gtgaaggtgc ttctttcggt     120
aacgctggtt gcttcaacgg ttcctccgtt gttccaatgt ccatgccagg aaacttgact     180
agcgttccaa agtggcttct tgacccaatg ggtccattgt ccatccgttt cagctacttt     240
ccaaccatca tgccttggtt gattcgtttc ttgcttgctg gaagaccaaa caaggtgaag     300
gagcaagcta aggcactccg taacctcatc aagtccactg tgcctttgat caagtccttg     360
gctgaggagg ctgatgctag ccaccttatc cgtcacgaag gtcaccttac cgtgtaccgt     420
ggagaagcag acttcgccaa ggaccgtgga ggttgggaac ttcgtcgtct caacggtgtt     480
cgtactcaaa tcctcagcgc tgatgcattg cgtgatttcg atcctaactt gtctcacgcc     540
tttaccaagg gaatccttat cgaagagaac ggtcacacca tcaacccaca aggtctcgtg     600
actctcttgt ttcgtcgttt catcgctaac ggtgagagt tcgtgtctgc tcgtgttatc     660
ggattcgaga ctgaaggtcg tgctctcaag ggtatcacca ccaccaacgg tgttcttgct     720
```

```
gttgatgcag ctgttgttgc agctggtgca cactccaagt ctcttgctaa ctcccttggt    780
gatgacatcc cattggatac cgaacgtgga taccacatcg tgatcgccaa cccagaagct    840
gctccacgta ttccaactac cgatgcttct ggaaagttcc ggtccaaatt tgtttacatt    900
gtgtccaaat tcggctgat ttggacttcc ctag                                 934
```

<210> SEQ ID NO 34
<211> LENGTH: 1224
<212> TYPE: DNA
<213> ORGANISM: Artificial sequence
<220> FEATURE:
<221> NAME/KEY: misc_feature
<222> LOCATION: (1)..(1224)
<223> OTHER INFORMATION: Amplified fragment

<400> SEQUENCE: 34

```
tctccacaat ggcttcctct atgctctctt ccgctactat ggttgcctct ccggctcagg     60
ccactatggt cgctcctttc aacggactta agtcctccgc tgccttccca gccacccgca    120
aggctaacaa cgacattact tccatcacaa gcaacggcgg aagagttaac tgcatgcagg    180
tgtggcctcc gattggaaag aagaagtttg agactctctc ttaccttcct gaccttaccg    240
attccggtgg tcgcgtcaac tgcatgcagg ccatggctga gaaccacaag aaggttggta    300
tcgctggagc tggaatcgtt ggtgtttgca ctgctttgat gcttcaacgt cgtggattca    360
aggttacctt gattgatcca aacccaccag gtgaaggtgc ttctttcggt aacgctggtt    420
gcttcaacgg ttcctccgtt gttccaatgt ccatgccagg aaacttgact agcgttccaa    480
agtggcttct tgacccaatg ggtccattgt ccatccgttt cagctacttt ccaaccatca    540
tgccttggtt gattcgtttc ttgcttgctg gaagaccaaa caaggtgaag gagcaagcta    600
aggcactccg taacctcatc aagtccactg tgcctttgat caagtccttg ctgaggagg     660 ctgatgctag ccaccttatc cgtcacgaag gtcaccttac cgtgtaccgt ggagaagcag    720
acttcgccaa ggaccgtgga ggttgggaac ttcgtcgtct caacggtgtt cgtactcaaa    780
tcctcagcgc tgatgcattg cgtgatttcg atcctaactt gtctcacgcc tttaccaagg    840
gaatccttat cgaagagaac ggtcacacca tcaacccaca aggtctcgtg actctcttgt    900
ttcgtcgttt catcgctaac ggtggagagt tcgtgtctgc tcgtgttatc ggattcgaga    960
ctgaaggtcg tgctctcaag ggtatcacca ccaccaacgg tgttcttgct gttgatgcag   1020
ctgttgttgc agctggtgca cactccaagt ctcttgctaa ctcccttggt gatgacatcc   1080
cattggatac cgaacgtgga taccacatcg tgatcgccaa cccagaagct gctccacgta   1140
ttccaactac cgatgcttct ggaaagttcc ggtccaaatt tgtttacatt gtgtccaaat   1200
ttcggctgat ttggacttcc ctag                                          1224
```

<210> SEQ ID NO 35
<211> LENGTH: 888
<212> TYPE: DNA
<213> ORGANISM: Artificial sequence
<220> FEATURE:
<221> NAME/KEY: misc_feature
<222> LOCATION: (1)..(888)
<223> OTHER INFORMATION: Amplified fragment

<400> SEQUENCE: 35

```
aaggttggta tcgctggagc tggaatcgtt ggtgtttgca ctgctttgat gcttcaacgt     60
cgtggattca aggttacctt gattgatcca aacccaccag gtgaaggtgc ttctttcggt    120
```

-continued

| | |
|---|---|
| aacgctggtt gcttcaacgg ttcctccgtt gttccaatgt ccatgccagg aaacttgact | 180 |
| agcgttccaa agtggcttct tgacccaatg ggtccattgt ccatccgttt cagctacttt | 240 |
| ccaaccatca tgccttggtt gattcgtttc ttgcttgctg aagaccaaa caaggtgaag | 300 |
| gagcaagcta aggcactccg taacctcatc aagtccactg tgcctttgat caagtccttg | 360 |
| gctgaggagg ctgatgctag ccaccttatc cgtcacgaag gtcaccttac cgtgtaccgt | 420 |
| ggagaagcag acttcgccaa ggaccgtgga ggttgggaac ttcgtcgtct caacggtgtt | 480 |
| cgtactcaaa tcctcagcgc tgatgcattg cgtgatttcg atcctaactt gtctcacgcc | 540 |
| tttaccaagg gaatccttat cgaagagaac ggtcacacca tcaacccaca aggtctcgtg | 600 |
| actctcttgt tcgtcgttt catcgctaac ggtggagagt tcgtgtctgc tcgtgttatc | 660 |
| ggattcgaga ctgaaggtcg tgctctcaag ggtatcacca ccaccaacgg tgttcttgct | 720 |
| gttgatgcag ctgttgttgc agctggtgca cactccaagt ctcttgctaa ctcccttggt | 780 |
| gatgacatcc cattggatac cgaacgtgga taccacatcg tgatcgccaa cccagaagct | 840 |
| gctccacgta ttccaactac cgatgcttct ggaaagttcc ggtccaaa | 888 |

<210> SEQ ID NO 36
<211> LENGTH: 1178
<212> TYPE: DNA
<213> ORGANISM: Artificial sequence
<220> FEATURE:
<221> NAME/KEY: misc_feature
<222> LOCATION: (1)..(1178)
<223> OTHER INFORMATION: Amplified fragment

<400> SEQUENCE: 36

| | |
|---|---|
| tctccacaat ggcttcctct atgctctctt ccgctactat ggttgcctct ccggctcagg | 60 |
| ccactatggt cgctcctttc aacggactta agtcctccgc tgccttccca gccacccgca | 120 |
| aggctaacaa cgacattact tccatcacaa gcaacgcgg aagagttaac tgcatgcagg | 180 |
| tgtggcctcc gattggaaag aagaagtttg agactctctc ttaccttcct gaccttaccg | 240 |
| attccggtgg tcgcgtcaac tgcatgcagg ccatggctga gaaccacaag aaggttggta | 300 |
| tcgctggagc tggaatcgtt ggtgtttgca ctgctttgat gcttcaacgt cgtggattca | 360 |
| aggttacctt gattgatcca aacccaccag gtgaaggtgc ttctttcggt aacgctggtt | 420 |
| gcttcaacgg ttcctccgtt gttccaatgt ccatgccagg aaacttgact agcgttccaa | 480 |
| agtggcttct tgacccaatg ggtccattgt ccatccgttt cagctacttt ccaaccatca | 540 |
| tgccttggtt gattcgtttc ttgcttgctg aagaccaaa caaggtgaag gagcaagcta | 600 |
| aggcactccg taacctcatc aagtccactg tgcctttgat caagtccttg gctgaggagg | 660 |
| ctgatgctag ccaccttatc cgtcacgaag gtcaccttac cgtgtaccgt ggagaagcag | 720 |
| acttcgccaa ggaccgtgga ggttgggaac ttcgtcgtct caacggtgtt cgtactcaaa | 780 |
| tcctcagcgc tgatgcattg cgtgatttcg atcctaactt gtctcacgcc tttaccaagg | 840 |
| gaatccttat cgaagagaac ggtcacacca tcaacccaca aggtctcgtg actctcttgt | 900 |
| tcgtcgttt catcgctaac ggtggagagt tcgtgtctgc tcgtgttatc ggattcgaga | 960 |
| ctgaaggtcg tgctctcaag ggtatcacca ccaccaacgg tgttcttgct gttgatgcag | 1020 |
| ctgttgttgc agctggtgca cactccaagt ctcttgctaa ctcccttggt gatgacatcc | 1080 |
| cattggatac cgaacgtgga taccacatcg tgatcgccaa cccagaagct gctccacgta | 1140 |
| ttccaactac cgatgcttct ggaaagttcc ggtccaaa | 1178 |

TRANSGENIC SUGAR BEET PLANT EXPRESSING CP4/EPSPS ENZYME ACTIVITY

CROSS-REFERENCE TO RELATED APPLICATION

U.S. application Ser. No. 09/434,039 is a continuation of U.S. application Ser. No. 09/182,117 filed Oct. 29, 1998, which has issued as U.S. Pat. No. 6,204,436, which claims the benefit of provisional application No. 60/112,003 filed Oct. 31, 1997.

BACKGROUND OF THE INVENTION

1. Field of the Invention

The present invention relates to transgenic sugar beet plants capable of tolerating herbicide treatment with glyphosate as active ingredient.

2. Background of the Related Art

Weeds in sugar beet fields are a major problem for the farmer. They compete with the crop thus reducing yield. Today, no single herbicide is able to effectively control all weeds without harming the sugar beet crop itself (Miller et al, J. Sugar Beets Res. 26: 3–4, 1989). In practice, farmers use mixtures of herbicides, which also reduce growth of the crop. Meanwhile the number of weed species having developed resistance to said herbicides continues to increase (Schweizer et al, J. of Sugar Beet Research 28: 1–23, 1991) thereby aggravating the problem of weed control in sugar beet fields.

Roundup® is a broadspectrum, environmentally preferable herbicide inhibiting the growth of both weed and crop species. In the context of the present invention one liter of a herbicidal Roundup® solution comprises 360 g of its active ingredient (a.i.) glyphosate (the common name of N-phosponomethyl-glycine) which is taken up by foliage. So far no glyphosate resistant weed has developed in over 20 years of use (Holt et al., Annu. Rev. Plant Physiol., 1993); additionally no natural tolerance to glyphosate has been found in sugar beet. However, pre-emergence use of Roundup® seems to be more efficient for weed control in sugar beet fields than a combination of herbicides often used in sugar beet agriculture, consisting of phenmediphan, metamitron and ethofumesate (Madsen et al, Weed Res. 35: 105–111, 1995).

Glyphosate inhibits the biosynthesis of aromatic amino acids, through irreversible binding to 5-enolpyruvylshikimate-3-phosphate synthase (epsps). Within the chloroplast this enzyme catalyzes the reaction of shikimate-3-phosphate and phosphoenolpyruvate to form 5-enolpyruvylshikimate-3-phosphate and phosphate. Approximately one week after application of the herbicide, visible effects can be seen including wilting, yellowing followed by complete browning, deterioration of plant tissue, and decomposition of the roots.

To impart glyphosate tolerance to crop species, focus has been on the introduction into plants of epsps genes capable of increasing glyphosate tolerance. Besides plants bacteria and fungi naturally express epsps enzyme activity. The cp4/epsps from Agrobacterium sp. CP4 was found to confer tolerance to glyphosate (Barry et al., "Inhibitors of Amino Acid Biosynthesis: Strategies for Imparting Glyphosate Tolerance to Crop Plants", in: Biosynthesis and Molecular Regulation of Amino Acids in Plants, Singh et al (eds), American Society of Plant Physiologists, pages 139–145, 1992). Introduction of the cp4/epsps gene into soybean and oilseed rape yielded tolerance to foliar application of the herbicide under field conditions (Delannay et al., Crop Sci. 35: 1461–1467, 1995; Padgette et al., Crop Sci. 35: 1451–1461, 1995).

Glyphosate oxidase reductase (gox) isolated from Achromobacter sp. strain LBAA (Barry et al., supra) degrades glyphosate into aminomethyl phosphonic acid, a compound non-toxic for the plant. A combination of the cp4/epsps and glyphosate oxidase (gox) genes has been successfully used to obtain transgenic wheat (Zhou et al., Plant Cell Rep. 15: 159–163, 1995) tolerant to glyphosate.

SUMMARY OF THE INVENTION

The object of the present invention is to provide sugar beet plants which tolerate glyphosate in doses sufficiently high to effect optimal herbicidal activity. Such plants can be further improved by backcrossing with elite sugar beet lines to optimize agronomic properties such as yield, pathogen resistance, etc.

Sugar beets may be transformed using Agrobacterium tumefaciens mediated transformation (Fry et al, Third international congress of plant mol. biol., Tuscon, Ariz., USA; D'Halluin et al, Bio/Technology 10: 309–314, 1992; Konwar, J. Plant Biochem & Biotech 3: 37–41,1994). Agrobacterium-mediated transformation often results in more than one copy of the T-DNA being integrated into the plant's genome. The gene to be integrated is preferably introduced into the T-DNA such that it becomes located close to the T-DNA right border which, contrary to the left border, will almost always be transferred to the plant.

Plants according to the present invention tolerate treatment with more than about 3×6 liters of the herbicide Roundup® per hectar (about 18 liters per hectar). The total standard dose to obtain good weed control varies between 4 and 6 liters per hectare, depending on weed pressure. At these concentrations herbicide treatment exerts no detectable effect on plant vigour and leaf chlorosis. The tolerance exhibited by the plants according to the invention is conferred by a transgenically expressed cp4/epsps enzyme activity. A preferred embodiment of the present invention has been deposited with the National Collections of Industrial and Marine Bacteria Limited (NCIMB), 23 St Machar Drive, Aberdeen AB2 1RY, Scotland UK, on Oct. 24, 1997, under the Accession No. 40905. This deposit will be maintained in the NCIMB depository, which is a public depository, for a period of 30 years, or 5 years after the most recent request or for the effective life of the patent, whichever is longer, and will be replaced if it becomes nonviable during that period. Additionally, Applicant has satisfied all the requirements of 37 C.F.R §§1.801–1.809, including providing an indication of the viability of the sample. Applicant imposes no restriction on the availability of the deposited material from the NCIMB; however, Applicant has no authority to waive any restriction imposed by law on the transfer of biological material or its transportation in commerce.

The present invention thus relates to a sugar beet plant including the descendants thereof expressing cp4/epsps enzyme activity. In particular the invention relates to a sugar beet plant including the descendants thereof tolerating the treatment with about 4 to about 18 liters Roundup® per hectar.

Plants according to the present invention can be obtained by routine Agrobacterium mediated transformation using a transformation vector comprising between right and left T-DNA border sequences a piece of DNA as described in SEQ ID NO: 5 encoding i.a. cp4/epsps.

It was surprisingly found within the scope of the present invention, that a transformation event (RRMax) lacking left and right T-DNA border sequences within the transgenic genome and resulting in deletion of a considerable part of the transformation vector DNA while retaining the cp4/epsps encoding DNA provides superior glyphosate tolerance. In particular a piece of DNA as characterized by SEQ ID NO: 1 is found integrated into a highly repetitive region of the genome simlutaneously replacing part of said repetitive genomic sequence. The genomic DNA directly adjacent to that part of the transgene sequence which in the transformation vector used is linked to the T-DNA right border sequence, has the sequence given in SEQ ID NO: 2. The genomic DNA directly adjacent to the other end of the integrated transgenic DNA has the sequence given in SEQ ID NO: 3. The complete DNA sequence of the newly formed genomic DNA arrangement is given in SEQ ID NO: 4.

Accordingly, the present invention relates to a sugar beet plant including the descendents thereof wherein DNA characterized by the nucleotide sequence of SEQ ID NO: 1 forms part of the plant's genome and said nucleotide sequence preferably replaces highly repetitive DNA sequences within the plant's genome.

Preferred herein is a sugar beet plant including the descendents thereof wherein those parts of the genome directly linked to said nulceotide sequence are characterized by the nucleotide sequences of SEQ ID NO: 2 and SEQ ID NO: 3, respectively.

The herbicide tolerance engineered into the transgenic seeds and plants mentioned above are passed on by sexual reproduction or vegetative growth and can thus be maintained and propagated in descendant plants. Generally said maintenance and propagation make use of known agricultural methods developed to fit specific purposes such as tilling, sowing or harvesting. As the growing crop is vulnerable to attack and damages caused by insects or infections, measures are undertaken to control plant diseases, insects, nematodes, and other adverse conditions to improve yield. These include mechanical measures such a tillage of the soil or removal of infected plants, as well as the application of agrochemicals such as fungicides, gametocides, nematicides, growth regulants, ripening agents and insecticides.

Use of the herbicide tolerance of the transgenic plants and seeds according to the invention can further be made in plant breeding which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Thus, the transgenic seeds and plants according to the invention can be used for the breeding of improved plant lines which for example increase the effectiveness of conventional methods such as herbicide or pestidice treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof. Customarily used protectant coatings comprise compounds such as captan, carboxin, thiram (TMTD®), methalaxyl (Apron®), and pirimiphos-methyl (Actellic®). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods such as the methods exemplified above which are characterized by the use of transgenic plants, transgenic plant material, or transgenic seed according to the present invention.

In another embodiment, the present invention relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

The invention further relates to a commercial bag containing Roundup® tolerant sugar beet seed capable of expressing cp4/epsps, together with lable instructions for the use thereof. Preferred within this invention is a commercial bag comprising seed of a transgenic plant comprising stably integrated into its genome a piece of DNA having the nucleotide sequence depicted in SEQ ID NO: 1.

The transformation methodology employed can be summarized as follows:

(a) transforming in vitro grown sugar beet cotyledons using *Agrobacterium tumefaciens* with a vector comprising a piece of DNA encoding cp4/epsps such as described in SEQ ID NO: 5;

(b) regenerating shoots in the presence of glyphosate;

(c) transferring the shoots to soil in the greenhouse;

(d) treating plantlets with glyphosate;

(e) visually grading plant vigour and leaf chlorosis;

(g) selecting completely normal plants with normal vigour and leafes uneffected by glyphosate treatment; and (h) propagating the selected plants using conventional breeding techniques.

In particular shoots are regenerated in the presence of about 0.1 to about 10 mM, preferably about 1 mM glyphosate after 8–12 weeks of selection. Each transgenic shoot is further propagated into ten copies which can optionally be analyzed for the presence of the cp4/epsps transgene using polymerase chain reaction (PCR) before it is transferred to the greenhous for rooting. Light conditions in the greenhouse are 16 hours of light and 8 hours of darkness with a temperature of 22±2° C. At the three to four leaf stage, the plantlets are sprayed with an aqueous solution of Roundup® at a dose of 0.1 to 20 liters, preferably 1 liter per hectar. Visual injury ratings for plant vigour and plant chlorosis based on a scale from 0 (dead plant) to 9 (completely uneffected plant) are taken on individual plants 2 weeks after glyphosate application. Ratings of 0 to 3 are characteristic of susceptible plants. Ratings of 3 to 7 indicate a low to intermediate level of tolerance, and ratings of 8 or 9 indicate good levels of tolerance. In particular the the ratings have the following meaning:

| | |
|---|---|
| 9 | Unaffected plant identical to untreated control |
| 8 | Only very small necrosis on the tips of the leaves with less than 5% of the leaf area affected and yellow |
| 7 | Very small necrosis on the tips of the leaves which start to curl; less than 5% of the leaf area are affected and yellow |
| 6,5,4 | Increasing necrosis and leaf curl; leaves are becoming smaller than normal |
| 3,2 | No or very limited leaf growth; all leaves are curled and affected by necrosis |
| 1 | No growth of the plant; up to 5% of the plant stay green |
| 0 | Dead plant |

To collect data from field trials plants with normal vigour and uneffected by glyphosate treatment (rating 9) are further propagated or bred by convential techniques.

Transformation is preferably performed using a Ti vector comprising a piece of DNA with the sequence given in SEQ ID NO: 5 containing the cp4/epsps and gox genes both of which have been reported to confer tolerance to glyphosate in certain plant species, and the reporter gene uidA encoding the β-glucuronidase enzyme. The enhanced 35S promoter (Odell et al., Nature 313: 810–812, 1985) is linked to the uidA gene, the figworth mosaic virus (FMV) promoter (Gouwda et al., J. Cell. Biochem. Suppl. 13D: 301, 1989) to the cp4/epsps and gox genes. Upstream of the cp4/epsps and the gox genes a transit peptide (Gasser et al., J. Biol. Chem. 263:4280–4289, 1988) is inserted to achieve targeting of both of the proteins to the chloroplast.

One transformation event which was generated in accordance with the present invention is surprisingly found to be uneffected by doses of up to about 3×6 liters (about 18 liters) of the herbicide Roundup® per hectar. Molecular analysis reveals that

- there is a single copy of transgenic DNA integrated at a single locus;
- the integrated DNA encodes cp4/epsps and corresponds to truncated vector DNA;
- the integrated DNA replaces a piece of genomic DNA and has the sequence shown in SEQ ID NO: 1;
- the genomic DNA directly adjacent to the integrated DNA is characterized by the sequences of SEQ ID NO: 2 and SEQ ID NO: 3 resulting in the new genomic sequence arrangment of SEQ ID NO: 4;
- the cp4/epsps and the uidA genes are intact whereas the gox gene is truncated;
- other vector sequences are not present in the transgenic plants.

Now that this information is available plants derived from one of the specific transformation events according to the invention can be easily distinguished from other sugar beet plants by means of PCR. Suitable primer pair combinations allow to specifically identify genomic DNA sequences which are only present in plants directly or indirectly resulting from identical transformation events. Such events are not in any way limited to those obtained by Agrobacterium-mediated transformation but may also result from biolistic transformation experiments.

The present invention thus further relates to a sugar beet plant including the descendents thereof characterized in that PCR amplification with its genomic DNA as template results in amplification of

- a 739 bp DNA fragment when using a pair of oligonucleotide primers characterized by the sequences of SEQ ID NO: 18 and SEQ ID NO: 21; or
- a 834 bp DNA fragment when using a pair of oligonucleotide primers characterized by the sequences of SEQ ID NO: 20 and SEQ ID NO: 24; or
- a 1057 bp DNA fragment when using a pair of oligonucleotide primers characterized by the sequences of SEQ ID NO: 17 and SEQ ID NO: 22; or
- a 1224 bp DNA fragment when using a pair of oligonucleotide primers characterized by the sequences of SEQ ID NO: 19 and SEQ ID NO: 25.

EXAMPLES

DETAILED DESCRIPTION OF THE INVENTION

The following examples further describe the materials and methods used in carrying out the invention and the subsequent results. They are offered by way of illustration, and their recitation should not be considered as a limitation of the claimed invention.

Example 1

Sugar Beet Transformation

Sugar beet of genotype A1012 is transformed with a vector containing a cp4/epsps and a gox gene capable of confering glyphosate tolerance, the nptII gene, which confers resistance to the antibiotic kanamycin and the reporter gene uidA encoding β-glucuronidase (GUS). The nptII and the uidA gene are functionally linked to the enhanced 35S promoter (Odell et al., Nature 313: 810–812, 1985) whereas the cp4/epsps and gox genes are under control of the the figworth mosaic virus (FMV) promoter (Gouwda et al., J. Cell. Biochem. Suppl. 13D: 301, 1989). Additionally the cp4/epsps and gox gene are linked to a transit peptide (Gasser et al., J. Biol. Chem. 263: 4280–4289, 1988) positioned 5' to target both proteins to the chloroplast. cp4/epsps and uidA make use uf the E9 3' terminator sequences whereas gox and nptII use the corresponding NOS 3' sequence. In vitro grown sugar beet (Beta vulgaris. L) are transformed using *A. tumefaciens*. Plants are regenerated as described by Fry et al. ("Genotype-independent transformation of sugarbeet using *Agrobacterium tumefaciens*", Third international congress of plant mol. biol., Tuscon, Ariz., USA.,1991) and Konwar (J. Plant Biochem & Biotech 3: 37–41, 1994) using glyphosate at a concentration of 1 mM as selection agent. In order to eliminate *A. tumefaciens* the cotyledons are three times incubated in MS medium containing 500 mg/lit cefotaxime (60 min at 45–50 rpm). Regenerated shoots are analyzed after 8–12 weeks of selection on 1 mM glyphosate, 500 mg/lit cefotaxime including passage to fresh media every third week. Each transgenic shoot is further micropropagated into ten copies, analyzed for the presence of the transgene, and transferred to the greenhouse for rooting.

Polymerase Chain Reaction (PCR) is used to verify the presence of the cp4/epsps gene. Twenty mg of plant material is collected in an eppendorf tube from regenerated in vitro shoots. Total DNA is extracted essentially according to Tai et al, Plant Mol. Biol. Rep 8: 297–303, 1990. Minor modifications are adding 500 µp of 100 mM Tris-HCl pH 8.0 containing 50 mM Na-EDTA, 1.25% SDS (W/V), 0.38% Na-Bisulfite (W/V), and 200 µg/ml proteinase K and incubating at 65° C. for two hours. Undissolved leaf material is hooked out and total DNA precipitated and frozen for 2 hours at -20° C. PCR is performed according to the instructions included with the Perkin-Elmer Gene-Amp PCR kit (Perkin-Elmer Corp.) using a modified 10×reaction buffer consisiting of 100 mM Tris-HCl pH 8.3, 500 mM KCl, 30 mM $MgCl_2$, 1.0% Nonidet P40 (W/V), 0.4 µM cresol red in 24% sucrose (W/V) and the Taq Start Antibody (Clontech). For amplifying cp4/epsps sequences the following primers are used (Shah et al., Science 233: 478–481, 1986):

5'-CAC CGG TCT TTT GGA AGG TGA AG-3' (SEQ ID NO: 6) and

5'-AAC GAG ACC CAT AAC GAG GAA GC-3' (SEQ ID NO: 7).

For amplifying a genomic internal control sequence (surA, surB) the following primers are used:

5'-AAA CAG TCC CGT GCA TCC CCA AC-3' (SEQ ID NO: 8) and

5'-GAC GCT CTC CTT GAT TCT GTC CC-3' (SEQ ID NO: 9).

No variation in transformation efficiency is seen between different binary plasmids. Micropropagated shoots are transferred to soil in the greenhouse. Light conditions in the greenhouse are 200 µmol $m^{-2}$ $sec^{-1}$, (Osram Power Star HQI-Z, 400 W), 16 hours of light, 8 hours of darkness, and a temperature of 22±2° C. At the three to four leaf stage plantlets derived from 260 independent transformants are treated with Roundup®. A calibrated sprayer is used to apply an aqueous solution of the herbicide at a dose of 1 lit per ha. (360 g.a.i.$l^{-1}$) ). Visual injury ratings for phytotoxic effects, based on a scale from 0 (complete leaf necrosis) to 9 (no visible effects) are taken on individual plants 2 weeks after glyphosate application. For 75 different transformants phytotoxic effects ranging from score 0–6 are detected. The other 185 (71%) transformants score 7 or more which means they show minor or no visible effects after treatment with the herbicide. Those are further crossed with non-transgenic sugar beets to produce F1 progeny for subsequent evaluation in field trials.

Field trials are performed to evaluate the different transformation events under field conditions. The plots consist of three rows, each row 9 meter long, with a distance between the rows of 0.5 meter. One individual transformant is drilled in each plot. After an initial Roundup® application of 1 lit per ha (360 g a.i.$l^{-1}$), at the cotyledon stage, to eliminate non-transgenic segregating plants, the rows are singled by hand, to a final stand of 1 plant per 20 centimeter. Each plot is divided in three parts that are treated independently. One plot is treated with the conventional herbicides metamitron 0.1 kg a.i.$ha^{-1}$, phenmediphan 0.2 kg a.i.$ha^{-1}$ and ethofumesate 0.1 kg a.i.$ha^{-1}$. The other plot is treated with 2 times 2 lit per ha (1440 g a.i.$l^{-1}$) of Roundup® and the third plot is treated with 2 times 4 liter (2880 g a.i.$l^{-1}$) of Roundup®. The plants are treated at the two leaf stage and at the four leaf stage. Two weeks after the last application, the plants are scored for phytotoxic effects due to herbicide application. Symptoms ranging from complete susceptibility to complete tolerance are found. Differences between scoring in the greenhouse and scoring in the field trial are observed. This is probably due to environmental differences between the greenhouse and the field trial including absence of UVB light under glass. There were no morphological or physiological changes between plants from plots treated with different doses of Roundup®, compared to treatments with a conventional herbicide mixture. Two transformants show high tolerance to Roundup® after treatment with 2 times 2 lit and 2 times 4 lit per ha.

After spraying with Roundup®, tolerance was measured by grading for plant vigour (Tr.vig) and leaf chlorosis (Tr.chl). The various grades have the following meaning:

9 . . . Unaffected plant identical to untreated control

8 . . . Only very small necrosis on the tips of the leaves with less than 5% of the leaf area affected and yellow 7 . . . Very small necrosis on the tips of the leaves which start to curl; less than 5% of the leaf area are affected and yellow 6,5,4 . . . Increasing necrosis and leaf curl; leaves are becoming smaller than normal 3,2 . . . No or very limited leaf growth; all leaves are curled and affected by necrosis 1 . . . No growth of the plant; up to 5% of the plant stay green 0 . . . Dead plant 22 different transformation events (Entry 1-22) and 1 non-transgenic control (Entry 23) are sprayed with 1+4+4 liters of Roundup®/Ha (Total 9 l/Ha). The results of the visual injury rating are given in the following table.

| Entry | Vigour Rating | Chlorosis Rating | |
|---|---|---|---|
| 1 | 9 | 9 | (RRMax) |
| 2 | 6 | 7 | |
| 3 | 2 | 3 | |
| 4 | 5 | 7 | |
| 5 | 9 | 8 | |
| 6 | 3 | 3 | |
| 7 | 7 | 7 | |
| 8 | 7 | 8 | |
| 9 | 4 | 6 | |
| 10 | 5 | 6 | |
| 11 | 5 | 5 | |
| 12 | 4 | 5 | |
| 13 | 9 | 9 | |
| 14 | 3 | 5 | |
| 15 | 4 | 4 | |
| 16 | 2 | 3 | |
| 17 | 1 | 1 | |
| 18 | 2 | 2 | |
| 19 | 6 | 8 | |
| 20 | 7 | 5 | |
| 21 | 4 | 5 | |
| 22 | 5 | 7 | |
| 23 | 0 | 0 | (non-transgenic control) |

Example 2

Copy Number of the Integrated Transgenic DNA

The copy number of the transgenic DNA integrated within the genome of the transformant with the highest glyphosate tolerance (RRMax) is determined by Southern blot analysis of restriction fragments extending beyond the right and left border sequences of the transformation vector used.

Genomic DNA from RRMax and a non-transgenic plant with the same genetic is isolated from 250 mg of freeze dried sugar beet leaf material according to Saghai-Maroof et al., Proc. Natl. Acad. Sci. USA 81:8014-8018, 1984. DNA of the transformation vector used serves as the positive control. 15 µg of DNA are digested with 120 units of restriction enzyme for 4 hours at 37° C. in a total volume of 400 µl. The digested DNA is precipitated and redissolved in a total volume of 50 µl. Digested DNA, positive plasmid control, and molecular marker size standard (Lambda digested with EcoRI and HindIII) are separated on a 0.8% agarose gel. DNA is visualized with ethidium bromide and a photograph including a ruler is taken. The DNA is then transferred onto a Hybond N+ membrane and hybridized to the probe as described by Ausubel et al. (eds.) in: "Current protocols in molecular biology", Green Publishing Associates, Inc. and John Wiley & Sons, Inc., New York, 1987.

Probes complementary to basepairs 975–1766 of the cp4/epsps gene sequence (SEQ ID NO: 5) and basepairs 7108–7535 of the gox gene sequence (SEQ ID NO: 5) are prepared by Polymerase Chain Reaction (PCR) wherein the transformation vector used serves as the template DNA for the reaction. The cp4/epsps probe is used to determine the number of inserts flanking the right border region. The gox probe is used to determine the number of inserts flanking the left border region. The PCR products are purified using the Geneclean II® Kit of BIO 101 (La Jolla, Calif.). Labelling of the probe with $^{32}P$ is achieved making use of the Megaprime™ DNA labelling system of Amersham International (Little Chalfont, UK).

Determination of copy number can be performed by analysis of genomic DNA flanking the right border region. Genomic DNA is digested with the restriction enzyme NcoI which cuts the plasmid derived sequences between the 35S promoter and the uidA gene and within the sugar beet genome. The membrane is probed with the internal PCR fragment from the cp4/epsps gene. After digestion with NcoI and hybridizing with the cp4/epsps probe, a single band of 4.7 kb is detected in RRMax. This demonstrates a single copy of transferred DNA at a single locus.

Determination of copy number can also be performed by analysis of genomic DNA flanking the left border region. Genomic DNA is digested with the restriction enzyme HindIII which cuts the plasmid derived sequences between the E9 3' terminator of the uidA gene and the FMV promoter of the gox gene and within the sugar beet genome. After digestion with HindIII and hybridizing with the gox probe, a single band of approximately 2.0 kb is detected for the transformant RRMax. Since the minimum expected fragment size is ≧4.4 kb, the result indicates a truncation of the plasmid DNA during the transfer into the genomic DNA of the plant. Nevertheless, the result confirms that only a single copy of transferred DNA is integrated at a single locus.

Example 3

Sequence Analysis of the RRMax Integration Site

Genomic RRMax DNA is isolated from 250 mg of freezed dried sugar beet leaf material according to Saghai-Maroof et al. supra. A λFIXII phage library with insert sizes of 9–23 kb in an XhoI cloning site is made (ordered with Stratagene) and probed with cp4/epsps and gox probes to screen for putative clones covering the integration event. A total of 25 phages are detected which hybridize to the cp4/epsps or the gox probe. Two clones are found to hybridize to the cp4/epsps probe and the gox probe, respectively. One of them is purified (Fritsch et al., 1987) and further evaluated by Southern blot analysis and PCR. It contains a 15–16 kb insert of genomic DNA including the transgenic DNA and the flanking sugar beet sequences. Said flanking sequences are amplified by PCR using a primer matching FMV promoter or gox gene sequences in combination with a primer matching a sequence in the λFIXII cloning cassette (detailed sequences are given in Table 1 below). The integrated DNA/sugar beet junction regions are sequenced by the Sanger dideoxy-mediated chain-termination method using Applied Biosystems, Model 373A,Version 2.1.1. The primers used for sequencing are given in Table 2.

TABLE 1

Primers used for the amplification of the border regions

| Primer | Sequence |
|---|---|
| #3 | 5'-CAAGAAGGTTGGTATCGCTG-3' (SEQ ID NO: 10) |
| #7 | 5'-TCTTTTGTGGTCGTCACTGCGTT-3' (SEQ ID NO: 11) |
| #8 | 5'-GCGAGCTCTAATACGACTCACTAT-3' (SEQ ID NO: 12) |
| #9 | 5'-CGCGAGCTCAATTAACCCTCACT-3' (SEQ ID NO: 13) |

TABLE 2

Sequencing primers

| Primer | Sequence | Description |
|---|---|---|
| S1 | 5'-TCTGTACCCTGACCTTGTTG-3' (SEQ ID NO: 14) | to sequence the flanking right border region |
| S3 | 5'-CGTGGATACCACATCGTGAT-3' (SEQ ID NO: 15) | to sequence the flanking left border region |
| S4 | 5'-ACCTTGGCTTGAAGTACTC-3' (SEQ ID NO: 16) | to sequence the flanking left border region |

Sequence analysis revealed that the transgenic DNA integrated in the genome of RRMax has the nucleotide sequence given in SEQ ID NO: 1. The integration start point lies between the right border sequence and the FMV promoter and terminates 897 basepairs downstream of the gox startcodon. Translational stop codons for the truncated gox gene can be found 130 and 235 basepairs downstream of the junction site. A HindIII site is identified 210 basepairs downstream and a transcriptional termination signal (AATAAA) 650 basepair downstream of the gox start codon. SEQ ID NO: 2 describes the DNA sequence of the genomic DNA directly linked to the right border region of the transgenic DNA and SEQ ID NO: 3 describes the DNA sequence of the genomic DNA directly linked to the left border region of the transgenic DNA.

Example 4

Characterization of the Transgenic DNA Integrated by RRMax

To further characterize the right border region, genomic DNA of RRMax and transformation vector DNA are digested with either restriction enzyme BamHI, HindIII, BclI or EcoRI. In southern blot analysis the cut DNA is probed with the cp4/epsps PCR fragment described in Example 2. Independent of the restriction enzyme used, digestion with the different restriction enzymes gives rise to a single fragment in Southern blot analysis. The size of the fragments detected are indicated in Table 3. The data demonstrate that a single copy of the DNA was transferred to the plant, and that the DNA transfer into the sugar beet plant resulted in complete transfer of the cp4/epsps gene. The results are in agreement with the results of the copy number determination in example 2 and the nucleotide sequence analysis of example 3.

TABLE 3

Southern blot fragment sizes

| Enzyme | RRMax | transformation vector |
|---|---|---|
| BamHI | >10 kb | 9.7 kb |
| HindIII | 2.4 kb | 2.4 kb |

TABLE 3-continued

Southern blot fragment sizes

| Enzyme | RRMax | transformation vector |
|---|---|---|
| BclI | 3.2 kb | 2.9 kb |
| EcoRI | 1.8 kb | 1.8 kb |

To further characterize the piece of transgenic DNA integrated, genomic DNA from RRMax is digested with either restriction enzyme NcoI, BamHI or HindIII. As a control Transformation vector DNA is digested with the same restriction enzymes. The blot is probed with a PCR amplified DNA fragment spanning basepairs 3796–4837 of the uidA gene in SEQ ID NO: 5. The size of the fragments detected is indicated in Table 4. Independent of restriction enzyme used, digestion with the different restriction enzymes gives rise to a single signal on the autoradiographic film demonstrating that the DNA insert has the same characteristics as the internal DNA of the transformation vector used.

TABLE 4

Southern blot fragment sizes

| Enzyme | transformation vector | RRMax |
|---|---|---|
| NcoI | 3.4 kb | 3.4 kb |
| BamHI | 3.2 kb | 3.2 kb |
| HindIII | 3.2 kb | 3.2 kb |

To further characterize the left border region, genomic DNA of RRMax and transformation vector DNA are digested with either restriction enzyme NcoI, BamHI, HindIII or EcoRI. In southern blot analysis the cut DNA is probed with the gox PCR fragment described in Example 2. The size of the fragments detected is indicated in Table 5. Independent of restriction enzyme used, digestion with the different restriction enzymes gives rise to a single fragment fragment on the autoradiographic film. Digestion with either restriction enzyme NcoI, BamHI or EcoRI is expected to identify an internal fragment of a known size. However, none of these restriction enzymes gives rise to such an internal fragment of the expected size. This indicates that the restriction sites for NcoI, BamHI, and EcoRI are absent in the transgenic plant. The results are in agreement with the results obtained by sequencing where it was found that the gox gene was only partly integrated in the plant. Digestion with restriction enzyme HindIII gives rise to a fragment of approximately 2 kb additionally confirming the sequencing data where a HindIII site is located downstream the gox gene in the genome. The results also show that a single copy of the transgenic DNA has been transferred to the plant. They correlates well to the primary results of the copy number determination in example 2 and the nucleotide sequence analysis in example 3. A single copy is integrated in the plant genome whereas the gox gene is partly deleted.

TABLE 5

Southern blot fragment sizes

| Enzyme | transformation vector | T9100152 |
|---|---|---|
| NcoI | 2.5 kb | 3.0 kb |
| BamHI | 2.9 kb | >10 kb |
| HindIII | 9.5 kb | 2.0 kb |
| EcoRI | 1.6 kb | 3.6 kb |

Example 5

Absence of Other Vector DNA Sequences

To verify the absence of oriV, ori-322, aad and nptII sequences in the transformation event RRMax southern blot analysis can be performed using restriction enzyme/probe combinations covering oriV, ori-322, aad and nptII.

Transformation vector DNA is digested with restriction enzyme NspI which cuts the plasmid at 17 sites. For the purpose of the analysis a NspI fragment covering oriV and a fragment covering ori-322 and aad are purified and used for Southern Blot analysis. A PCR amplified fragment with the nucleotide sequence given in SEQ ID NO: 26 is used to probe for nptII sequences. All fragments are purified with the Geneclean II® Kit of BIO 101 (La Jolla, Calif.). Labelling with $^{32}P$ is achieved with the Megaprime™ DNA labelling system of Amersham International (Little Chalfont, UK).

Genomic DNA of RRMax is digested with the restriction enzyme BamHI which cuts the transformation vector DNA at three sites, positioned at basepairs 2321, 5544 and 8413 of SEQ ID NO: 5. Hybridization of the corresponding southern transfer membrane with the probe covering oriV failed to detect a signal. It has to be concluded that oriV is not present in RRMax.

Hybridization of the corresponding southern transfer membrane with the probe covering ori-322 and aad failed to detect a signal. It has to be concluded that ori-322 and aad sequences are not present in RRMax.

Hybridization of the corresponding southern transfer membrane with the nptII probe also failed to detect a signal, which demonstrates that an nptII gene is not present in line RRMax.

Example 6

Stability of the RRMax Line

Digestion of genomic DNA with the restriction enzyme BclI and Southern blot analysis using the cp4/epsps gene as a probe are performed as described in Example 2. Four plants from generations 2 and 3, and five plants from generation 4 are used for this analysis. In addition, 3 non-transgenic plants are used as a negative control. Analysis of the primary transformation event results in a single fragment of 3.2 kb. Southern blot analysis of the progeny generations also results in a single fragment of 3.2 kb. If the introduced DNA is stably inherited from generation to generation, the same fragment of 3.2 kb is expected in all plants.

Digestion of genomic DNA with HindIII and Southern blot analysis using an internal fragment of the gox gene as a probe are performed as described in Example 2. Analysis of the primary transformation event results in a single fragment of 2.0 kb. Southern blot analysis of the progeny generations also results in a single fragment of 2.0 kb indicating stable inheritance of the trait.

Example 7

PCR characterization of RRMax

Genomic DNA of line RRMax is prepared as described in example 2. About 0.5 μg of DNA are used as template DNA in a PCR reaction using specific combinations of primers characterized by the sequences given in Table 6. Said specific combinations and the size of the fragment amplified are given in Table 7. Depending on the primer pair combination an annealing temperature between 55° C. and 65° C. is used in each of the 30 to 35 amplification cycles.

TABLE 6

Primer Sequences

| Primer | Sequence | Description |
|---|---|---|
| A | 5'-TCAACCTACAGCTGATTTGGACC-3' (SEQ ID NO: 17) | near the right border junction |
| B | 5'-GGACCGGAACGACAATCTGATC-3' (SEQ ID NO: 18) | near the right border junction |
| C | 5'-CTAGGGAAGTCCAAATCAGCCG-3' (SEQ ID NO: 19) | near the left border junction |
| D | 5'-TTTGGACCGGAACTTTCCAGAAG-3' (SEQ ID NO: 20) | near the left border junction |
| a | 5'-CTAACTTGCGCCATCGGAGAAAC-3' (SEQ ID NO: 21) | within the cp4/epsps gene |
| b | 5'-GACTTGTCACCTGGAATACGGAC-3' (SEQ ID NO: 22) | within the cp4/epsps gene |
| c | 5'-ATTCTTGAGCTCATCAAGCAGCC-3' (SEQ ID NO: 23) | within the cp4/epsps gene |
| e | 5'-AAGGTTGGTATCGCTGGAGCTG-3' (SEQ ID NO: 24) | within the gox sequences |
| f | 5'-TCTCCACAATGGCTTCCTCTATG-3' (SEQ ID NO: 25) | within the gox sequences |

| Combination | Size of amplified fragment |
|---|---|
| A + a | 757 bp (SEQ ID NO:28) |
| A + b | 1057 bp (SEQ ID NO:29) |
| A + c | 2352 bp (SEQ ID NO:30) |
| B + a | 739 bp (SEQ ID NO:27) |
| B + b | 1039 bp (SEQ ID NO:31) |

-continued

| Combination | Size of amplified fragment |
|---|---|
| B + c | 2334 bp (SEQ ID NO:32) |
| C + e | 934 bp (SEQ ID NO:33) |
| C + f | 1224 bp (SEQ ID NO:34) |
| D + e | 888 bp (SEQ ID NO:35) |
| D + f | 1178 bp (SEQ ID NO:36) |

What is claimed is:

1. A transgenic sugar beet plant expressing cp4/epsps enzyme activity, wherein PCR amplification of said sugar beet plant genomic DNA as template results in the amplification of a 739 bp DNA fragment having the nucleotide sequence given in SEQ ID NO: 27 when using a pair of oligonucleotide primers consisting essentially of the sequences SEQ ID NO: 18 and SEQ ID NO: 21, wherein said amplification is conducted under an annealing temperature of between about 55° C. and 65° C.

2. A transgenic sugar beet plant expressing cp4/epsps enzyme activity, wherein PCR amplification of said sugar beet plant genomic DNA as template results in the amplification of a 888 bp DNA fragment having the nucleotide sequence given in SEQ ID NO: 35 when using a pair of oligonucleotide primers consisting essentially of the sequences SEQ ID NO: 20 and SEQ ID NO: 24, wherein said amplification is conducted under an annealing temperature of between about 55° C. and 65° C.

3. A transgenic sugar beet plant expressing cp4/epsps enzyme activity, wherein PCR amplification of said sugar beet plant genomic DNA as template results in the amplification of a 1057 bp DNA fragment having the nucleotide sequence given in SEQ ID NO: 29 when using a pair of oligonucleotide primers consisting essentially of the sequences SEQ ID NO: 17 and SEQ ID NO: 22, wherein said amplification is conducted under an annealing temperature of between about 55° C. and 65° C.

4. A transgenic sugar beet plant expressing cp4/epsps enzyme activity, wherein PCR amplification of said sugar beet plant genomic DNA as template results in the amplification of a 1224 bp DNA fragment having the nucleotide sequence given in SEQ ID NO: 34 when using a pair of oligonucleotide primers consisting essentially of the sequences SEQ ID NO: 19 and SEQ ID NO: 25, wherein said amplification is conducted under an annealing temperature of between about 55° C. and 65° C.

5. The plant according to claim 1, 2, 3, or 4 wherein said genomic DNA comprises SEQ ID NO: 1.

6. The plant according to claim 5, wherein said nucleotide sequence replaces highly repetitive DNA sequences.

7. The plant according to claim 5, wherein the parts of the genome directly linked to the right and left borders of SEQ ID NO: 1 comprise SEQ ID NO: 2 and SEQ ID NO: 3, respectively.

8. The plant according to claim 1, 2, 3, or 4 wherein said genomic DNA comprises SEQ ID NO: 4.

9. Transgenic seed of a plant according to claim 1, 2, 3, or 4.

10. Seed of a plant according to claim 9 deposited under the accession number NCIMB 40905.

* * * * *